(12) United States Patent
Kauppi et al.

(10) Patent No.: US 7,351,861 B2
(45) Date of Patent: Apr. 1, 2008

(54) METHOD AND PROBE FOR IDENTIFYING BACTERIAL VIRULENCE MODIFYING AGENTS, AGENTS THUS IDENTIFIED, AND THEIR USE

(75) Inventors: Anna Maria Kauppi, Umeå (SE); Jan Mikael Christian Elofsson, Umeå (SE); Hans Olof Wolf-Watz, Umeå (SE); Olov Roland Nordfelth, Umeå (SE); Markus Kristoffer Dahlgren, Göteborg (SE)

(73) Assignee: Innate Pharmaceuticals AB, Umea (SE)

( * ) Notice: Subject to any disclaimer, the term of this patent is extended or adjusted under 35 U.S.C. 154(b) by 0 days.

(21) Appl. No.: 10/526,461

(22) PCT Filed: Sep. 4, 2003

(86) PCT No.: PCT/SE03/01381

§ 371 (c)(1),
(2), (4) Date: Oct. 27, 2005

(87) PCT Pub. No.: WO2004/022775

PCT Pub. Date: Mar. 18, 2004

(65) Prior Publication Data

US 2006/0134724 A1   Jun. 22, 2006

(30) Foreign Application Priority Data

Sep. 4, 2002   (SE) .................................. 0202613

(51) Int. Cl.
*C07C 233/00* (2006.01)
(52) U.S. Cl. ..................................................... 564/152
(58) Field of Classification Search .................... None
See application file for complete search history.

(56) References Cited

U.S. PATENT DOCUMENTS 6,136,541 A   10/2000   Demers et al.

FOREIGN PATENT DOCUMENTS

| GB | 2365426 A | | 2/2002 |
|---|---|---|---|
| WO | WO 98/07745 | | 2/1998 |
| WO | WO99/11262 | * | 3/1999 |
| WO | WO-02/43668 A2 | | 6/2002 |

OTHER PUBLICATIONS

Ciampa et al. STN search abstract.*
Leemann et al. STN search abstract.*
Ainscough et al. Journal of Inorganic Biochemistry 1999;77:125-133.*
Kidwai et al., Indian Journal of Chemistry, vol. 39B, pp. 458-461 (2000).
Srivastava et al., Pharmazie, vol. 45, , pp. 34-37 (1990).
Covello et al., "New iodine containing organic compounds. Nuovi iodorganici di sintesi; Idrossibenzanilidi iodurate, Iodinated hydroxybenzanilides"; Rendiconto dell'Accademia delle Scienze Fisiche e Matematiche, vol. 33, pp. 309-318 (Naples) (1966).
Ainscough et al., Journal of Inorganic Biochemistry , vol. 77, pp. 125-133 (1999).
National Library of Medicine (NLM), file Medline, PMID: 8173809, Forsberg, A: "In vivo expression of virulence genes of *Yersinia pseudotuberculosis*"; Infect Agents Dis Aug. 1993; 2(4); 275-8.
ASM Abstract Database 2002 General Meeting (May 19, 2002 through May 23, 2002) American Society for Microbiology, Vladimir Motin, et al.: "Genome-Wide Expressing Profiling of *Yersinia pestis* During Low-Calcium Response"; retrieved Apr. 4, 2003 from http://www.asmusa.org/memonly/abstracts/AbstractView.asp?AbstractID=62023.
Infection and Immunity, vol. 43(1); Jan. 1984; Ingrid Bolin, et al.; "Molecular Cloning of the Temperature-Inducible Outer Membrane Protein 1 of *Yersinia pseudotuberculosis*"; p. 72-78.
Molecular Microbiology, vol. 2(2); 1988; Ingrid Bolin, et al.; "The plasmid-encoded Yop2b protein of *Yersinia pseudotuberculosis* is a virulence determinant regulated by calcium and temperature at the level of transcription"; p. 237-245.
STN International, File Caplus, Caplus accession No. 1968:95469, Document No. 68:95469, Giuseppe Ciampa, et al.; "N-Substituted salicylamides. I. Halogenated 2-hydroxy-and 2-acetoxybenzanilides with antibacterial and antifungal activity"; Rendiconto dell'Academia delle Scienze Fisiche e Matematiche, Naples 1966, 33(Dec.), 386-95.
STN International, File Caplus, Caplus accession No. 1978:94851, Document No. 88:94851, "Anthelminticcompositions based on benzimidazoles"; FR, A, 2336931, 19770729.
STN International, File Caplus, Caplus accession No. 1979:16910, Document No.: 90:16910, E.M. Shilakadze, et al.; "Antituberculosis activity of beta- and gamma-pyridinecarboxylic acid phenylhydrazones and their manganese(II) and manganese(III) complexes"; Soobshcheniya Akademii Nauk Gruzinskoi SSR (1978), 91(1), 145-8, esp. compound RN=68639-26-9.
STN International, File Caplus, Caplus accession No. 1992:645585, Document No. 117:245585, Ivanovo Agricultural Institute: "Method for treatment of fascioliasis and monieziaosis in sheep"; SU, A1, 1715357, 19920228.
STN International, File Caplus, Caplus accession No. 1977:189559, Document No. 86:189559, Chinoin Gyogyszer es Vegyeszeti Termekek Gyara Rt., Hung.: "Salicylanilides"; BE, A1, 839873, 19760716.

(Continued)

Primary Examiner—Ralph Gitomer
Assistant Examiner—Bin Shen
(74) Attorney, Agent, or Firm—Dickstein Shapiro LLP

(57) ABSTRACT

A method for identifying antibacterial agents comprises depleting bacteria of a strain comprising a luxAB construct of $Ca^{2+}$, incubating the $Ca^{2+}$ depleted bacteria with an agent the antibacterial effect of which shall be determined, recording the light emitted by the bacteria upon addition of an aldehyde, the incubation being carried out at a temperature which is at least 10° C. higher than the temperature at which the light is emitted by the bacteria. Also disclosed are corresponding probes and antibacterial agents identified by the method.

6 Claims, 12 Drawing Sheets

OTHER PUBLICATIONS

STN International, File Caplus, Caplus accession No. 1985:487603, Document No.: 103:87603, J. M. Patel, et al.; "Studies on antitubercular and antibacterial agents: preparation of 1-(4-aminobenzoyl)-2-benzalhydrazine and 1-(4-(phenylthioureido)benzoyl)-2-substituted-benzalhydrazine"; Journal of the Indian Chemical Society; 1984; 61(8); 718-20.

STN International, File Caplus, Caplus accession No. 2002:298309, Document No. 137:169451, Vipin Kumar, et al.; "Synthesis and biological activities of 2-aryl-3-substituted benzamido-1,3-thiazolidin-4-ones" Indian Journal of Heterocyclic Chemistry; 2002; 11(13); 251-252.

J. Med. Chem.; vol. 41, 1998, Mark J. Macielag, et al.; "Substituted Salicylanilides as Inhibitors of Two-Component Regulatory Systems in Bacteria"; p. 2939-2945.

STN International, File Caplus, Caplus accession No. 2000:780229, Document No. 134:71527; Mazaahir, Kidwai, et al.; "Microwave assisted synthesis of new fungicidal pyrazoles"; Indian Journal of Chemistry; 2000; 39B(6); 458-461.

STN International, File Caplus, Caplus accession No. 2002:11847, Document No. 136:272653; K. Waisser, et al.; "2H-1,3-benzoxazine-2,4(3H)-diones substituted in position 6 as antimycobacterial agents"; Chemical Papers; 2001; 55(5); 323-334.

STN International, File Caplus, Caplus accession No. 1990:440580, Document No. 113:40580; R. P. Srivastava, et al.; "Synthesis of 2,5-disubstituted benzimidazoles, 1,3,4-thiadiazoles and 3,5-diiodosalicylanilides as structural congeners of rafoxanide and closantel"; Pharmazie (1990), 45(1), 34-7.

STN International, File Caplus, Caplus accession No. 1968:458923, Document No. 69:58923, Mario Covello, et al.; "New iodine containing organic compounds. Iodinated hydroxybenzanilides"; Rendiconto dell'Accademia delle Scienze Fisiche e Matematiche, Naples (1966), 33(Dec.), 309-18.

STN International, File Caplus, Caplus accession No. 2000:72793, Document No. 132:202643, Eric W. Ainscough, et al.; "Cytotoxicity of salicylaldehyde benzoylhydrazone analogs and their transition metal complexes: quantitative structure-activity relationships"; Journal of Inorganic Biochemistry (1999), 77(3-4), 125-133.

STN International, File Caplus, Caplus accession No. 1999:184132, Document No. 130:204267, Michael Brandt, et al.; "MPL-receptor ligands, process for their preparation, medicaments containing them, and their use for the treatment and prevention of thrombocytopenia and anemia"; PCT Int. Appl., 42 pp.

Database Registry; CAS RN:s 400054-03-7, 305338-58-3, 303084-13-1, 416883-56-2, and 341979-94-0.

STN International, File Caplus, Caplus accession No. 1998:147346, Document No. 128:213381, Janet R. Fraser, et al.; "Compositions and methods for treating infections using analogs of indolicidin"; PCT Int. Appl., 130 pp.

STN International, File Caplus, Caplus accession No. 1971:74914, Document No. 74:74914; A. P. Bekhli, et al.; "Synthesis of phenasal esters and their anthelmintic activity"; Meditsinskaya Parazitologiya i Parazitarnye Bolezni (1970), 39(5), 532-4.

* cited by examiner

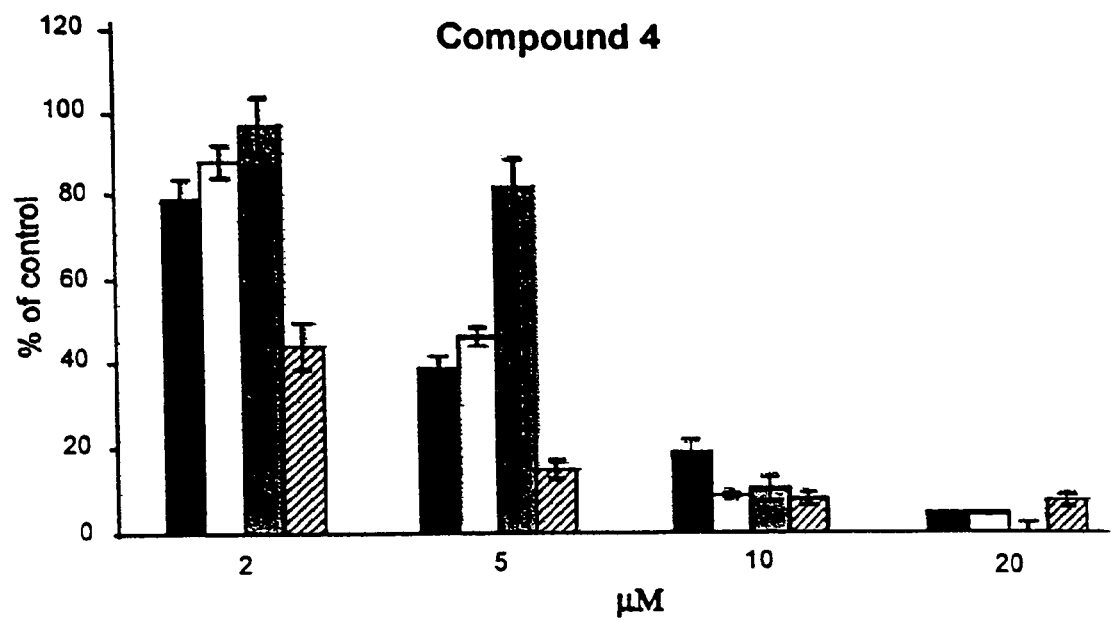
Fig. 5C
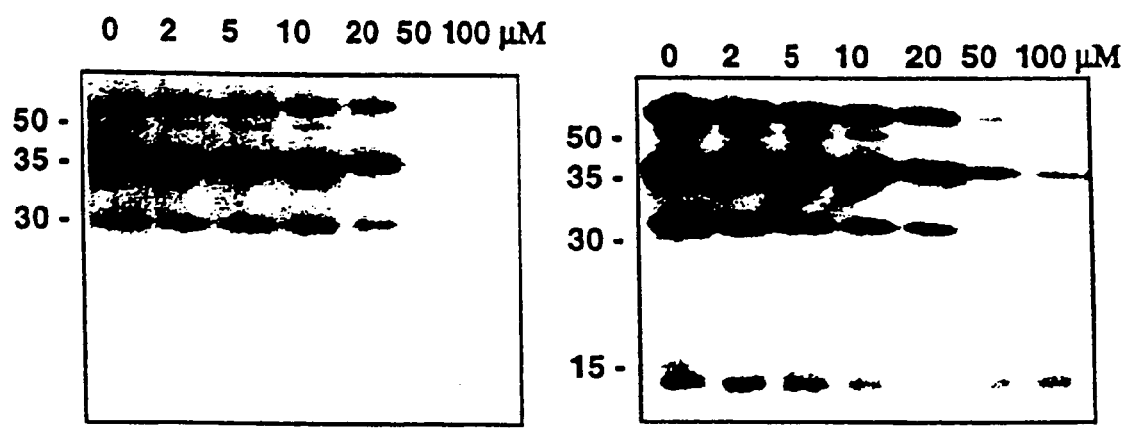
Fig. 6A
Fig. 6B

4

16

17

18

19

5

57

58

59

60

61

62

METHOD AND PROBE FOR IDENTIFYING BACTERIAL VIRULENCE MODIFYING AGENTS, AGENTS THUS IDENTIFIED, AND THEIR USE

FIELD OF THE INVENTION

The present invention relates to a method of assessing bacterial virulence modifying properties of chemical compounds and other agents including mixtures of agents, to a corresponding probe, to compounds possessing such properties identified by the method, and to their use.

BACKGROUND OF THE INVENTION

The use of powerful anti-microbial agents in combination with improved living conditions dramatically increased our capacity to fight off previously lethal infections. However, in the last ten years there has been a dramatic escalation in antibiotic resistance among microorganisms[1,2]. Such resistance proliferates readily in the bacterial kingdom through gene transfer, making the spread of resistance hard to control. Although a multitude of efforts to improve the situation have been made it is clear that additional approaches for microbe control are required[3]. One obvious way to address this challenge is to develop novel anti-microbial drugs. This task is however arduous and most antibacterial agents that have reached the market during the last decade are based on previously characterized structures with known modes of action i.e. a bactericidal or static effect. Recent advances in combinatorial chemistry[4-6], genomics[7,8], and screening technologies[9,10] however increase our capacity to identify novel bacterial targets and compounds that interfere with them. Combinatorial chemistry can indeed generate large numbers of diverse compounds but screening for novel agents from such libraries still mainly focus on agents that target microbial growth essentially in analogy with existing drugs[11]. An alternative is to identify compounds with a novel mode of action that target microbial virulence rather than growth[12,13]. Virulence includes events that enable the bacterium to enter the host, disarm the host's defence, multiply, and finally spread within the host or to a new host. Agents that target virulence are potentially effective antimicrobials but also apply less selective pressure for resistance. Moreover, compounds that perturb a virulence system can be employed as chemical probes to elucidate unknown features of bacterial virulence using a chemical genetics approach[14,15].

Recent studies have revealed that various pathogenic bacteria use related virulence systems, findings that contradict the long held paradigm that each bacterium has a unique mode of action. The type III secretion system of *Yersinia* represents the archetype of one of these systems in which the bacteria adhere to eukaryotic cells and inject a set of bacterial effector proteins, Yops (*versinia* outer proteins), that are capable of subverting the target cell[16,17]. This process involves a secretion of the Yops across the bacterial membranes and a subsequent translocation across the eukaryotic cell membrane. The genus *Yersinia* includes eleven known species of which *Y. pestis, Y. speudotuberculosis*, and *Y. enterocolitica* are pathogenic to humans of which *Y. pestis*, the causative agent of plague, is one of the most virulent bacteria known to man. These three species all share the tropism for lymphoid tissue and a capacity to evade the non-specific immune response. The processes of protein secretion and translocation represent attractive points of attack for novel antibacterial agents. The secretion apparatus is essential for the bacteria to evade the immune defence and it is possible that agents that inhibit the secretion can result in an antibacterial response without actually killing the bacteria. Moreover, several mammalian pathogens including *Yersinia* spp., *Salmonella* spp., *Shigella flexneri, Pseudomonas aureginosa*, enteropathogenic *Escherichia coli, Chlamydia* spp., and also plant pathogens like *Xanthomonas campestris, Erwinia* spp., *Pseudomonas syringae*, and *Ralstonia solanacearum* employ type III secretion systems that are crucial for virulence[18,19]. Some components of type III secretion systems in different species are interchangeable, which suggests evolutionary conservation and that data generated with one genus might also be valid for others. Thus, the type III secretion in gram negative bacteria is an important virulence system that constitutes an attractive drug target as well as a challenge for chemical genetics. The relevance of type III secretion in basic research and drug development is further stressed by the fact that multi-resistance strains have been found in *Y. pestis*[20,21] and that *Y. pestis* is a potential weapon in biological warfare and bioterrorism[22,23].

U.S. Pat. No. 6,136,542 discloses a method for screening agents that activate or inhibit type II secretion machinery in gram-negative bacteria. The method comprises exposing gram-negative bacterial cells to a sample of an agent to be screened, which cells contain a reporter gene, such as the luxAB gene, transcriptionally fused to a promoter of a gene activated or regulated by the type III secretion machinery, and detecting the presence or activity of the product of the reporter gene. The detection indicates whether the sample activates or inhibits type III secretion machinery. The gram-negative bacteria is selected from, i.a., *Yersinia*.

OBJECTS OF THE INVENTION

It is an object of the present invention to provide to a method for assessing bacterial virulence modifying properties of chemical compounds and other agents including mixtures of agents.

It is another object of the invention to provide a corresponding probe.

A further object of the invention is to provide agents capable of decreasing bacterial virulence.

Additional objects of the invention will become evident from the following description of the invention, a drawing comprising a number of figures, the description of preferred embodiments, and the appended claims.

SUMMARY OF THE INVENTION

According to the present invention is disclosed a method of identifying antibacterial agents. The method of the invention is based on a *Yersinia pseudotuberculosis* assay. It can be used to identify agents that target known or unknown components directly or indirectly, affecting the type III secretion machinery.

Thus, according to the invention is disclosed a method of screening for agents inhibiting or activating bacterial virulence, the method being carried out in absence of eukaryotic cells, comprising contacting a gram-negative bacterium culture depleted in $Ca^{2+}$, in particular a *Yersinia* species, comprising a luxAB reporter gene construct, with a potentially bacterial virulence inhibiting or activating agent, thereby forming a test suspension, manipulating the temperature of the test suspension and adding an aliphatic aldehyde to make the bacterium emit light, measuring the emitted light, comparing the amount of emitted light with the light emitted in absence of the bacterial virulence inhibiting or activating agent.

The method of the invention for identifying antibacterial agents comprises depleting bacteria of a strain comprising a luxAB construct of $Ca^{2+}$, incubating the $Ca^{2+}$ depleted bacteria with an agent the antibacterial effect of which shall be determined, recording the light emitted by the bacteria upon addition of an aldehyde such as decanal, the incubation being carried out at a temperature which is at least 10° C. higher than the temperature at which the light is emitted by the bacteria, preferably at least 15° C. higher. It is preferred for the strain to be a Yersinia sp. strain, in particular a Yersinia pseudotuberculosis strain. Preferred incubation and emission temperatures are about 37° C. and about 21° C., respectively. Agents having a useful antibacterial effect will inhibit, at a concentration of 50 µM, the luciferase light signal from pIB29EL by at least 40%, more preferred by at least 60%, most preferred by at least 80%.

More specifically, the method of the invention comprises the following steps:

providing a Yersinia sp. bacterial strain comprising a luxAB construct;

propagating the strain at room temperature in a $Ca^{2+}$ depleting medium to obtain a suspension of $Ca^{2+}$ depleted of bacteria containing the luxAB construct;

dissolving a measured amount of a sample of an antibacterial agent candidate in water, a mixture of water and of an organic solvent or an organic solvent;

organic solvent to prepare a solution of the agent;

combining the solution of the agent with an aliquot of the bacterial suspension to obtain a test suspension;

incubating the test suspension at a first temperature for a selected period of time;

raising the temperature of the test suspension to a second temperature;

continuing incubation at the second temperature for a selected period of time;

lowering the temperature of the test suspension to a third temperature;

continuing the incubation at the third temperature for a selected period of time;

adding n-decanal or a functionally equivalent aldehyde to the test suspension;

measuring light emitted from the test suspension over a period of time at the third temperature;

quantifying the light emitted;

calculating an antibacterial activity based on the quantity of emitted light.

Preferably the first and third temperature is from 20° C. to 26° C., most preferred about 21° C., while the second temperature is about 37° C. Decanal or a functionally equivalent aldehyde is preferably added to the test suspension in form of an aqueous emulsion. At the first hand, the compound to be tested or a salt thereof is dissolved in water. If its solubility in water is to low, it may be dissolved in an organic solvent, preferably DMSO, or a mixture of water and an organic solvent. Preferred concentrations of test compound in the test suspension are from 10 µg per mL to 100 µg per mL.

It is, of course, also possible to identify compounds that increase the level of virulence factors (activators) by the method of the invention which has to be slightly modified by substituting the $Ca^{2+}$ depleted medium by a medium which is not $Ca^{2+}$ depleted. An activator will counteract the inhibition of the type III secretion machinery by LcrQ and provide for light emission which can be measured.

According to a preferred aspect of the invention the bacterial strain comprising the luxAB construct is a Yersinia pseudotuberculosis strain or a mutant strain thereof, in particular a non-virulent strain, such as the pIB29EL strain. Other useful strains are pIB29AL, pIB102EL, pIB102AL, pIB102FL, and pIB102FΔhlhL.

According to the invention there is thus disclosed a probe for identifying antibacterial agents comprising the Yersinia pseudotuberculosis strain pIB29EL. According to the invention there is also disclosed a probe for identifying antibacterial agents comprising the Yersinia pseudotuberculosis strains pIB29AL, pIB102EL, pIB102AL. Other probes according to the invention for identifying antibacterial agents comprise the Yersinia pseudotuberculosis strains pIB102FL and pIB102FΔhlhL.

Regulation of the type III secretion machinery in Y. pseudotuberculosis is relatively well understood. Its modest virulence compared to Y. pestis makes it a suitable candidate for assay development. In addition, it was recently established that Y. pestis has evolved from Y. pseudotuberculosis. The components of the virulence system, i.e. the effector proteins and proteins involved in regulation and secretion, are encoded by a ~70 kb virulence plasmid. Although many functions of the Yersinia type III secretion and its regulation are poorly understood, results from different laboratories have contributed to provide a broad picture of secretion-related events[16,18,19]. When the bacteria enter the host and sense a temperature shift to 37° C. they prepare for battle by producing ~20 Ysc (yersinia secretion) proteins that form the secretion channel spanning the bacterial inner and outer membranes. This temperature shift also results in expression of chaperones, Sycs (specific yop chaperones) which, at a later stage, protect the Yersinia outer proteins, Yops, and deliver them to the Ysc apparatus. Expression of the Ysc proteins and Sycs is regulated by the temperature triggered protein LcrF. On the other hand, low LcrQ suppress the expression of the Yops, which thus are present in small amounts only, until the bacterium comes in direct contact with a eukaryotic cell. Contact with β-integrin on the eukaryotic target cell triggers the secretion of LcrQ which results in strong Yop production. The cognate Sycs then bind to the newly produced Yops and deliver them to the Ysc apparatus. In parallel a poorly understood chain of events results in formation of a pore in the eukaryotic cell membrane. The structure of this pore is unknown but several Yersinia proteins including LcrV, YscF, YopB, and YopD are known to be crucial for this process. The Yops are secreted through the Ysc machinery and then translocated through the pore into the cytoplasm of the eukaryotic cell. In the eukaryotic cell the six different Yops, YopE, YopH, YpkA, YopJ, YopM, and YopT specifically target eukaryotic processes such as phagocytosis and production of proinflammatory cytokines. The production and secretion of Yops have been found to be $Ca^{2+}$ dependent in vitro. At 26° C. Yersinia grows both in the presence and absence of $Ca^{2+}$, whereas millimolar concentrations of $Ca^{2+}$ are required for growth at 37° C. In $Ca^{2+}$ depleted medium at 37° C. a metabolic downshift is observed and growth is halted after a few generations. Most important, this is accompanied by LcrQ secretion and subsequent strong expression and secretion of the Yops in absence of eukaryotic cells. $Ca^{2+}$ depletion in vitro thus mimics external stimuli that the bacteria encounter in the host. The role of this $Ca^{2+}$ dependence in vivo has however not been clarified. The simplified regulatory model for Syc and Yop expression given in FIG. 1A was used to design reporter gene contructs for screening. As reporter for transcription luciferase from Vibrio Harveyi[25]

was selected. In the presence of n-decanal this enzyme oxidises flavine mononucleotide which results in the emission of light of a wavelength of 490 nm. The emitted light is detected with a light-sensitive charge-coupled device (CCD) camera. In this way the expression of protein is monitored. All strains used are *Y. psedotuberculosis* serotype III (YPIII) and in the following text strains are only labelled with the name of the virulence plasmid. Following a previously reported strategy[26] the luciferase encoding gene, luxAB, was cloned to be under the control of the effector protein YopE promoter on the virulence plasmid. The construct was introduced in both wild-type bacteria (pIB102)[27] and a non-virulent strain (pIB29)[28], in which the gene for the effector protein YopH has been replaced with a resistance marker. The resulting strains pIB102EL[26] and pIB29EL were found to exhibit secretion properties, including in vitro temperature and $Ca^{2+}$ regulation, virtually identical with those of wild-type *Y. pseudotuberculosis* (data not shown). Thus, according to the invention, it is possible, by using a bacterium, in particular a *Yersinia* species, with the luxAB reporter gene construct, to monitor processes regulating secretion specific transcription and screen for inhibitors or activators in absence of eukaryotic cells by manipulating the temperature and the $Ca^{2+}$ concentration as schematically shown in FIG. 1B. The cloning strategy of the invention was also used to prepare control strains in which luxAB was cloned to be downstream of the promoter for yerA, the specific yop chaperone for YopE. In the resulting wild-type (pIB102AL) and non-virulent (pIB29AL) strains the luciferase expression was found to be dependent on temperature but independent of $Ca^{2+}$ concentration.

In a general procedure an over-night culture is diluted and dispensed in, for instance, 96-well plates. After initial incubation at room temperature which allows the culture to attain stable growth, the temperature of the plate including the wells is brought to 37° C. In the absence of $Ca^{2+}$ growth is suppressed and secretion is activated whereas, in the presence of $Ca^{2+}$, secretion remains at a inactive level while the bacteria continue to grow. The plate is then cooled to room temperature, that is, about 21° C., and kept at that temperature for a selected period of time, after which n-decanal is added and the emission of light is measured with a camera. The assay conditions including initial bacterial density, incubation times, etc. have been optimised (data not shown) to give a robust and reliable system which is useful for the identification of secretion inhibitors. A typical result from an assay with bacteria alone (pIB29EL) in absence or presence of $Ca^{2+}$ is shown in FIG. 2. The agent to be tested for secretion inhibiting properties, usually an organic compound, is dissolved in an amount of a suitable solvent that does not interfere with the method, preferably DMSO. According to the invention it was found that sufficient DMSO tolerance of the assay was obtained by keeping the DMSO concentration below two percent by volume of the aqueous test culture suspension to avoid a non-specific reduction of the light emission (data not shown). When employing the assay for screening purposes the presence of an inhibiting or activating effect can be established within a time period of about six to seven hours.

Since the assay is based on a transcriptional readout, agents perturbing not only the type III secretion system have the potential to result in reduction of light emission. To address the scope and limitations of the assay a number of well-studied antibiotics with known modes of actions were evaluated. As summarized in Table 1 carbenicillin, streptomycin, nalidixic acid, and polymyxin B all result in a dose-dependent inhibition of light-emission with the indicated $IC_{50}$ values. These data clearly illustrate that the assay; despite that only a short period of time is allowed for growth (<3 h), efficiently can detect bactericidal agents acting on a variety of bacterial targets.

According to a preferred aspect the method of the invention can also be used to screen for agents specifically targeting the type III secretion system. A panel of polyclonal rabbit serum antibodies against a set of relevant *Yersinia* proteins that putatively are present on the bacterial surface and directly or indirectly regulate the secretion was evaluated. The rabbit serum was however found to contain one or more factors that enhanced light-emission both in presence and absence of $Ca^{2+}$ (data not shown). In spite of that antibodies against YopB were capable of completely inhibiting light-emission (data not shown). YopB is a *Yersinia* outer protein believed to be involved in formation of pores in the eukaryotic cell membrane. To further study this inhibitory effect a monoclonal mouse antibody against YopB was tested and found to abrogate light emission when added to the assay solution up to 2 h after start of the experiment (FIG. 3). After the shift to 37° C. the secretion system gets activated but an increased YopB expression is not detectable until after approximately one hour, indicating that addition of the YopB neutralizing antibody results in an immediate inhibitory response. Thus, agents that specifically target one component of the type III secretion machinery can effect complete suppression of Yop expression. This suggests a therapeutic window for antibodies against virulence factors in the *Yersinia* type III secretion system.

The assay of the invention can be used to screen for agents targeting many different bacterial functions. In the first place the assay allows compounds that interfere with the type III secretion system to be detected. The assay is well suited for high-throughput screening of large compound collections. Compounds that interfere with the secretion system have potential both as drug candidates and molecular probes for functional studies of the type III secretion system in *Yersinia* and other gram-negative bacteria. Furthermore, a powerful feature of this assay is that it also can be used to identify activators of the system. Such compounds will be useful for investigations aimed at understanding the regulation of the system. Screening of a 9,400 compound library by the method identified a number of compounds which inhibit type III secretion at concentrations that do not prevent bacterial growth.

Several of the proteins that constitute the Ysc TTS system for Yop secretion have homologs in the secretion system used for assembly of the flagellum[18]. It is possible that compound that target Yop secretion target other type III secretion mechanisms e.g. flagellum assambly and motiliy. In order to study the possibility for inhibitors of Yop TTS to inhibit TTS flagellum assembly, bacterial motility and Yop transcription in presence of a compound according the invention were investigated. The experiments were carried out in six-well plates with $Ca^{2+}$ depleted migration agar containing different concentrations of the compound. Motility was found to be inhibited to 10, 40, 60, and 80% at 5, 10, 20, and 50 μM, respectively, of the compound of the invention.

According to the invention there are thus disclosed agents which affect bacterial virulence but do not have a detrimental effect of bacterial growth. The bacterial virulence-affecting agents of the invention are agents which interfere with the type III secretion system in *Yersinia*.

In particular, according to the invention, there are disclosed agents which decrease bacterial virulence. More particularly the agents of the invention decrease expression of bacterial virulence factors while not substantially affecting bacterial growth.

The agents of the invention capable of decreasing bacterial virulence comprise the structural element R—CO—NH—S-T, wherein R is aromatic or heteroaromatic carbon, S is zero or —N═CH, and T is unsubstituted or substituted aryl including heteroaryl.

According to a first preferred aspect of the invention the agents decreasing bacterial virulence are amides of the general formula I

wherein
A is substituted or unsubstituted aryl or heteroaryl;
B is —X—Y, wherein X is zero or —N═CH— and Y is selected from unsubstituted aryl, unsubstituted heteroaryl, mono-, di- and tri-substituted aryl, mono-, di- and tri-substituted heteroaryl, with the proviso that, if X is —N═C—H—, Y is 2-hydroxyaryl.

If A is substituted aryl or heteroaryl, it is preferred to be mono- or disubstituted by one or more of halogen, nitro, hydroxy, alkoxy, $C_1$-$C_6$ alkyl, $C_1$-$C_6$ alkenyl, halogen being preferably selected from Cl, Br, I and, independently, alkoxy preferably being acetoxy.

It is preferred for Y to be selected from aryl and heteroaryl substituted with one or several of halogen, $C_1$-$C_6$ alkyl, $C_1$-$C_6$ alkenyl, halogen being preferably being selected from F, Cl, Br.

According to another preferred aspect of the invention the agents decreasing bacterial virulence are amides of the general formula I

wherein
A is substituted or unsubstituted aryl, heteroaryl, substituted or unsubstituted aryloxy or carbamyl;
B is —X—Y, wherein X is zero, —N═CH— or —CO— and Y is selected from unsubstituted aryl, unsubstituted heteroaryl, mono-, di- and tri-substituted aryl, mono-, di- and tri-substituted heteroaryl, with the proviso that, if X is —N═C—H—, Y is 2-hydroxyaryl.

If A is substituted aryl or heteroaryl, it is preferred to be mono- or disubstituted by one or more of halogen, nitro, hydroxy, alkoxy, $C_1$-$C_6$ alkyl, $C_1$-$C_6$ alkenyl. It is preferred for Y to be selected from aryl and heteroaryl substituted with one or several of halogen, $C_1$-$C_6$ alkyl, $C_1$-$C_6$ alkenyl.

Preferred compounds of the general formula I are shown in FIGS. 7-11.

It is also preferred for a compound of the invention to inhibit, at a concentration of 50 μM, the luciferase light signal from pIB29EL by at least 40%, more preferred by at least 60%, most preferred by at least 80%.

Activity and physical data of preferred compounds of the invention are listed in Tables 2A-2C.

The inhibitory agents of the invention can be used in the treatment of infections caused by gram negative bacteria. The treatment comprises administering to a person suffering from such infection an antibacterially effective amount of an agent of the invention. Administration can be in any adequate form, such as, for example per-oral, IV or topical. The compounds of the invention can be incorporated in pharmaceutical compositions for such administration, e.g., tablets and capsules for oral administration, solutions for intravenous and intramuscular administration, and ointments for topical administration.

A person skilled in the art will appreciate that the antibacterial agents of the invention are not antibacterial agents in the classical sense but are agents that modify the virulence of bacteria and thereby exhibit antibacterial effect.

DESCRIPTION OF THE FIGURES

The invention will now be explained in more detail by reference to preferred embodiments illustrated by a number of Figures showing.

Figure 2A:
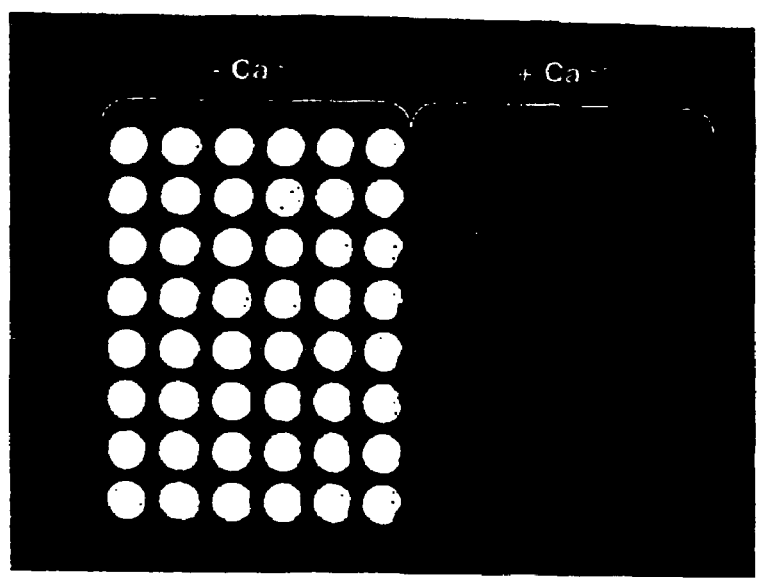
Figure 2B:
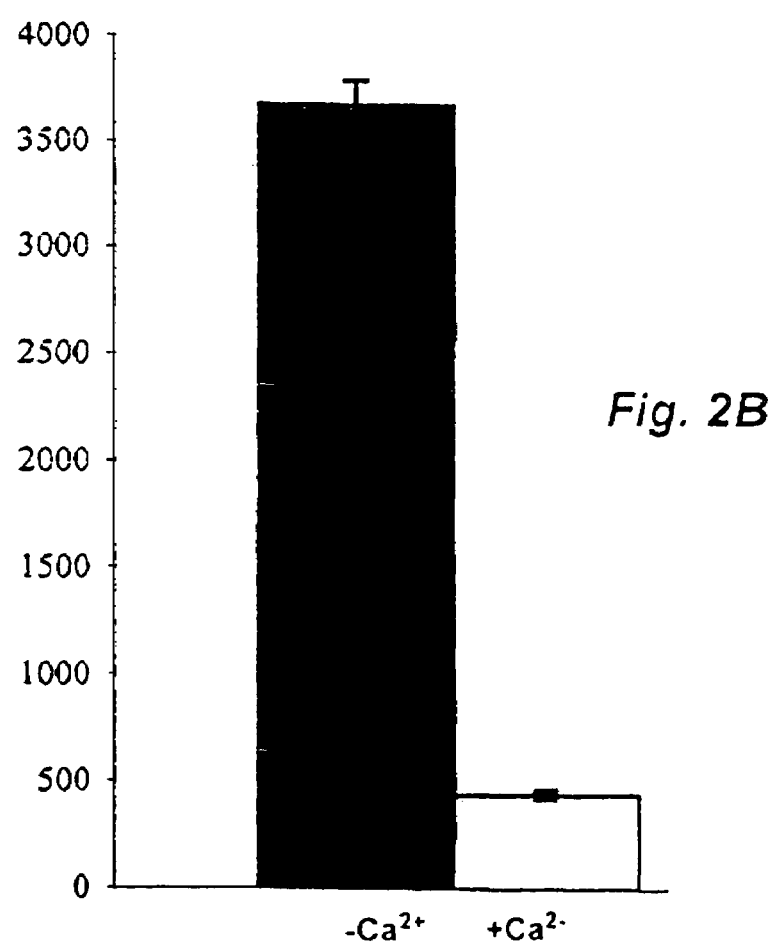
Figure 3:
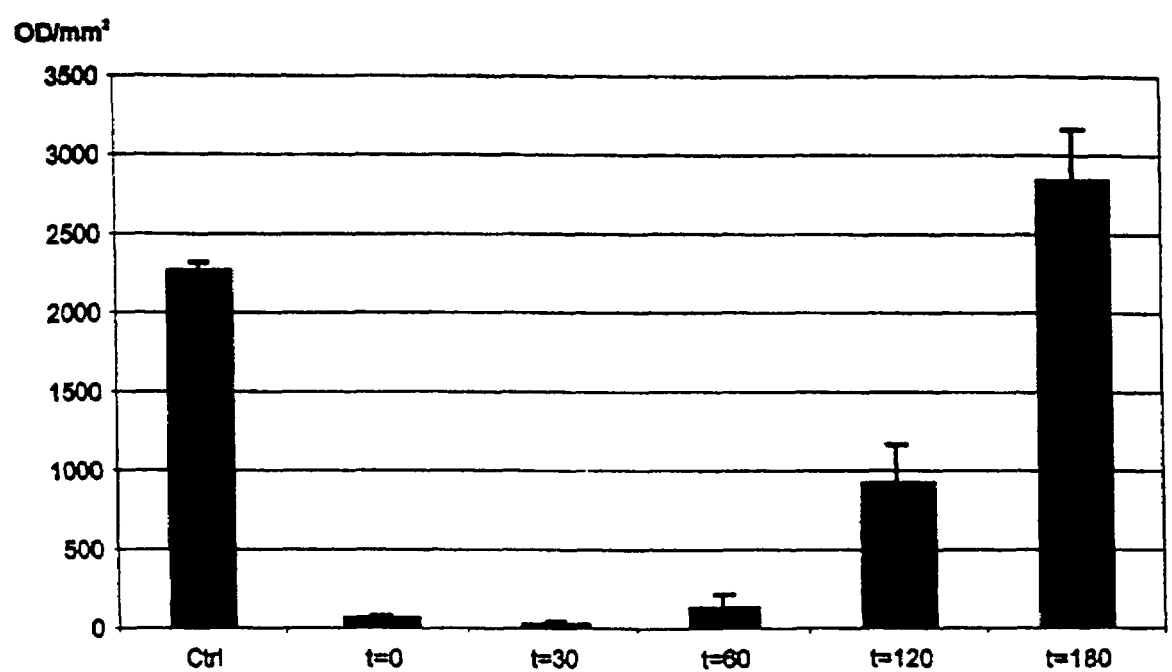
Figure 4A:
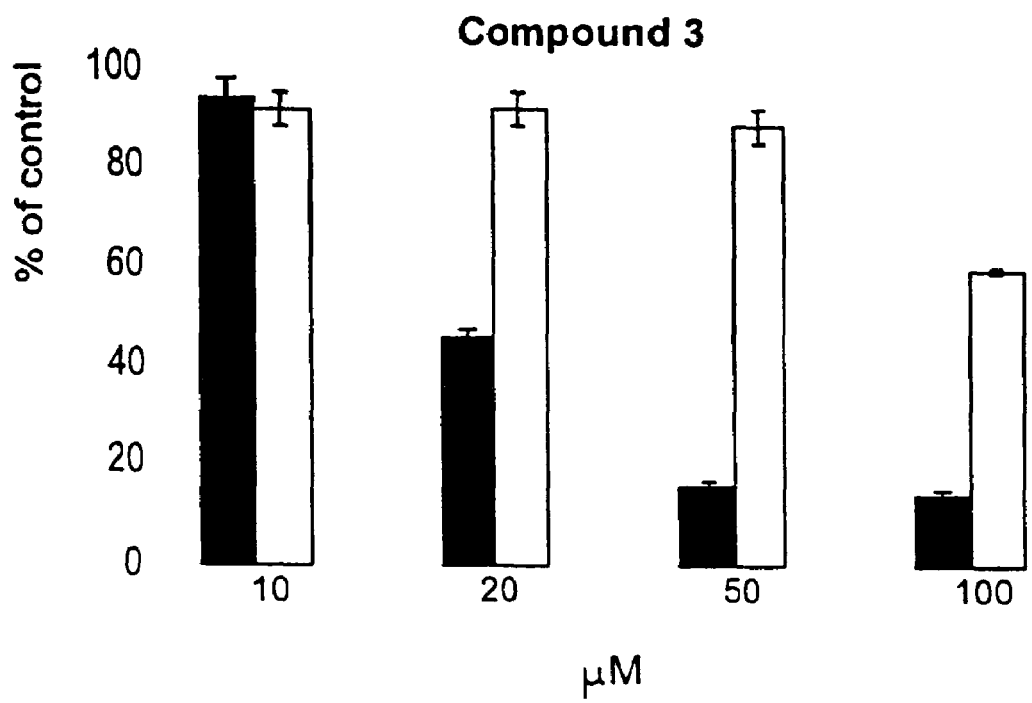
Figure 4B:
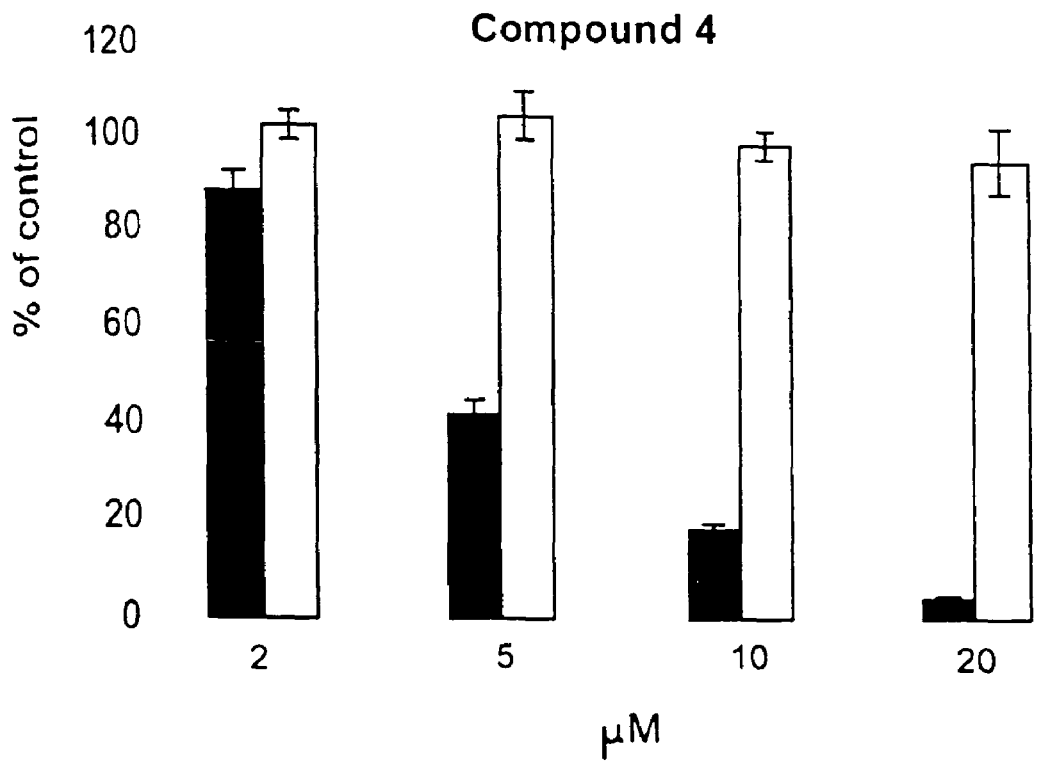
Figure 4C:
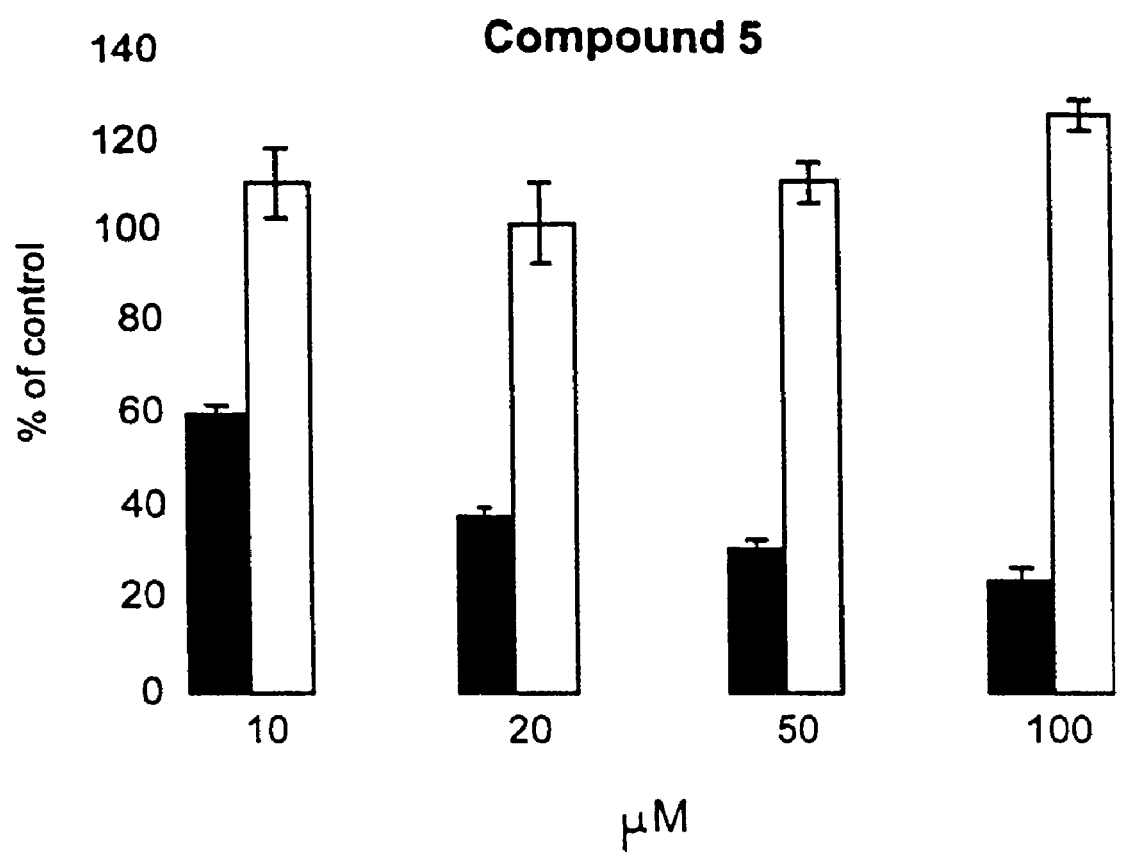
Figure 5A:
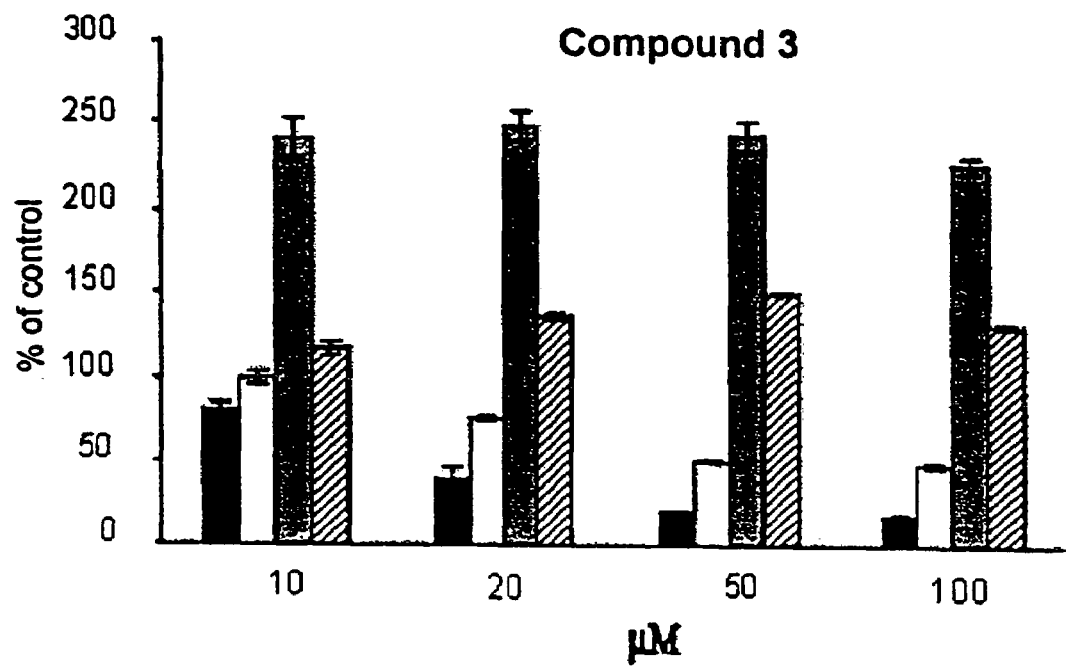
Figure 5B:
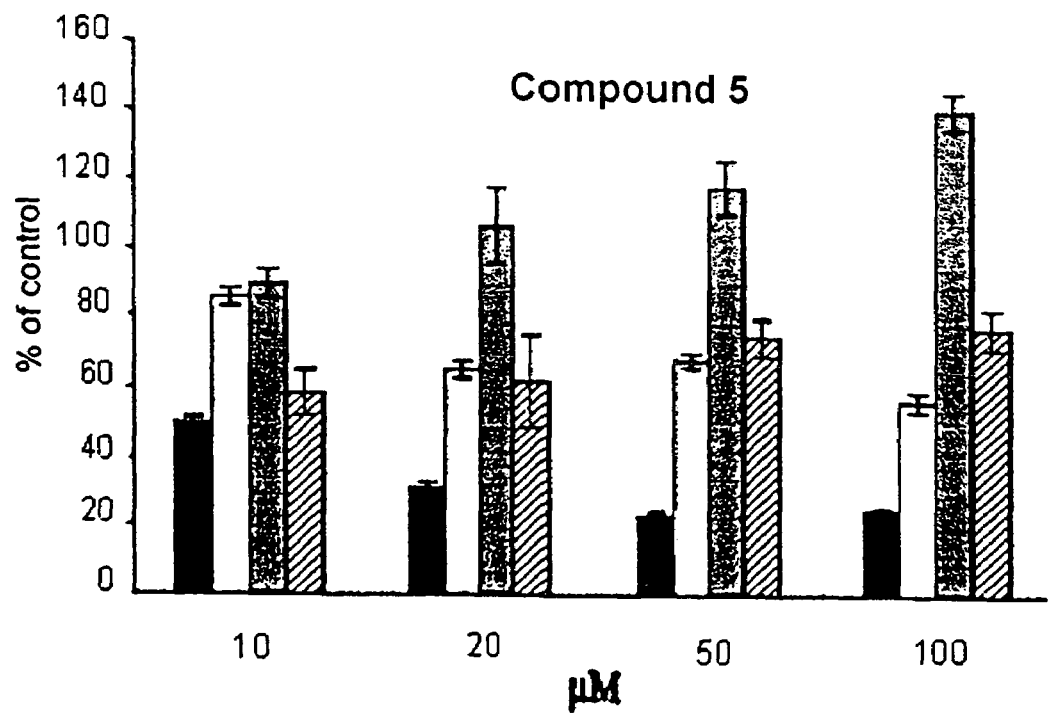
Figure 7:
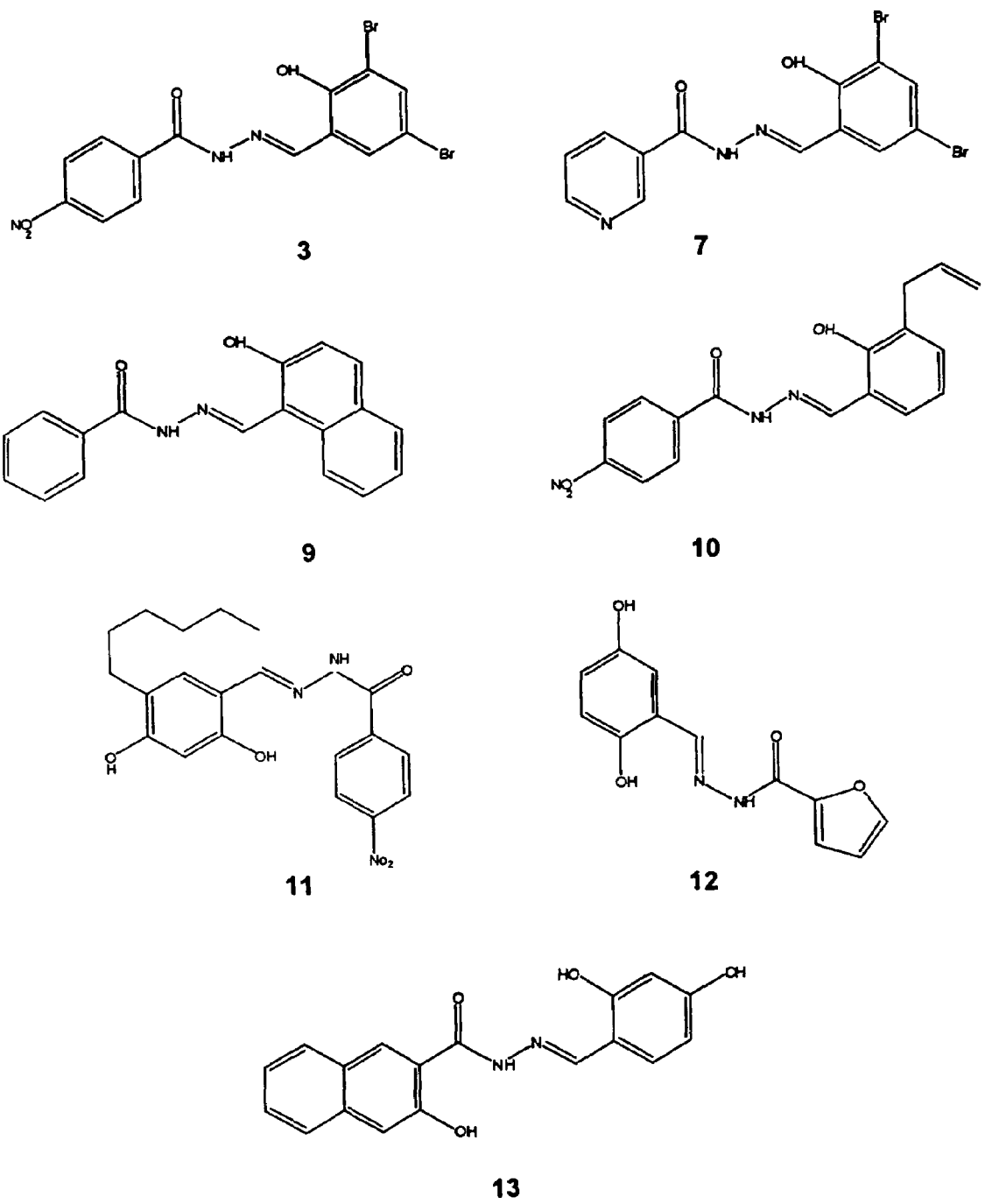
Figure 8:
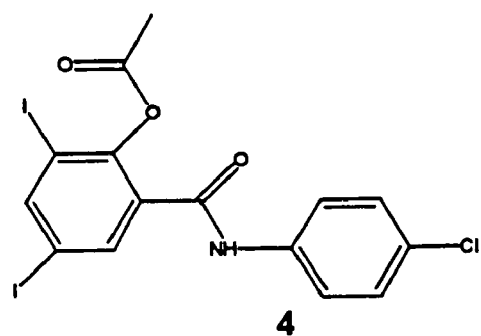
Figure 8:
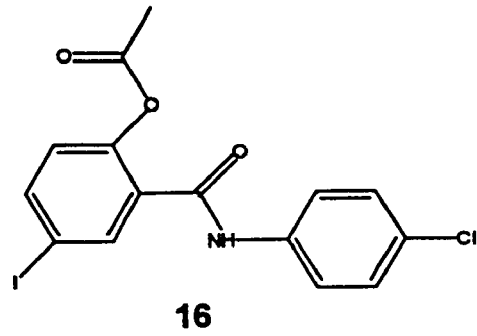
Figure 8:
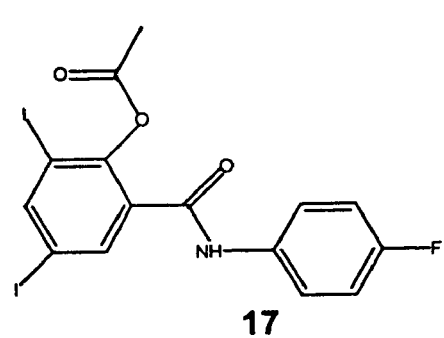
Figure 8:
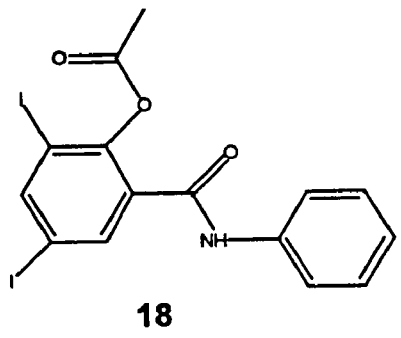
Figure 8:
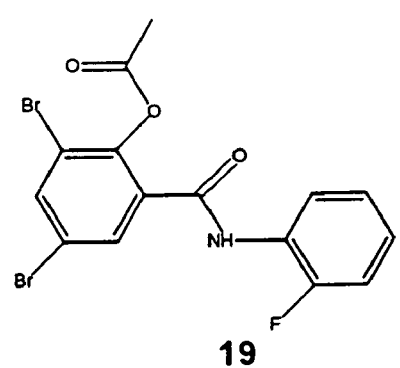
Figure 8:
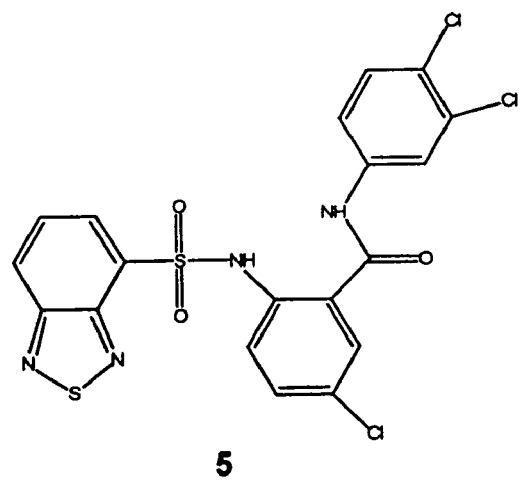
Figure 9:
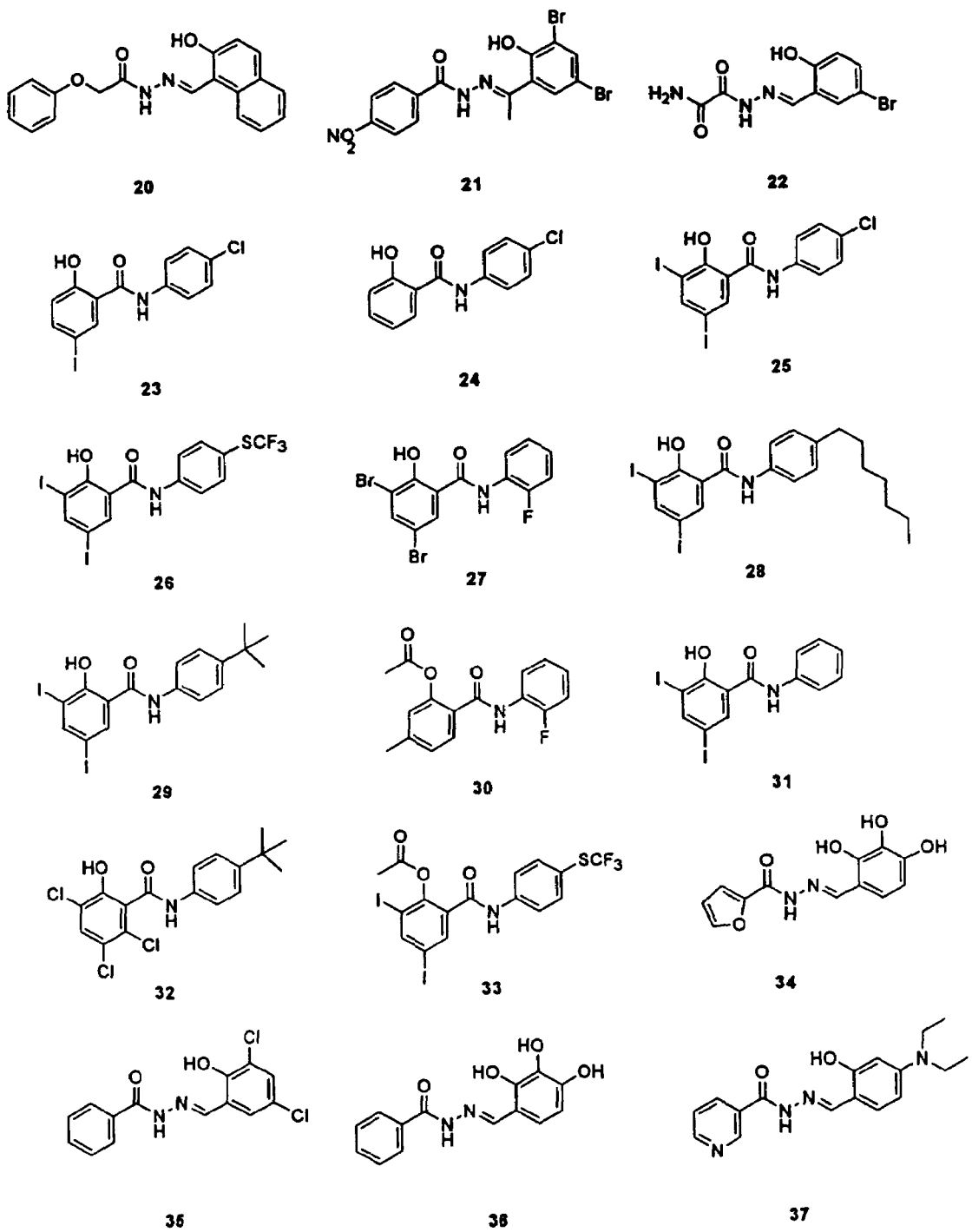
Figure 10:
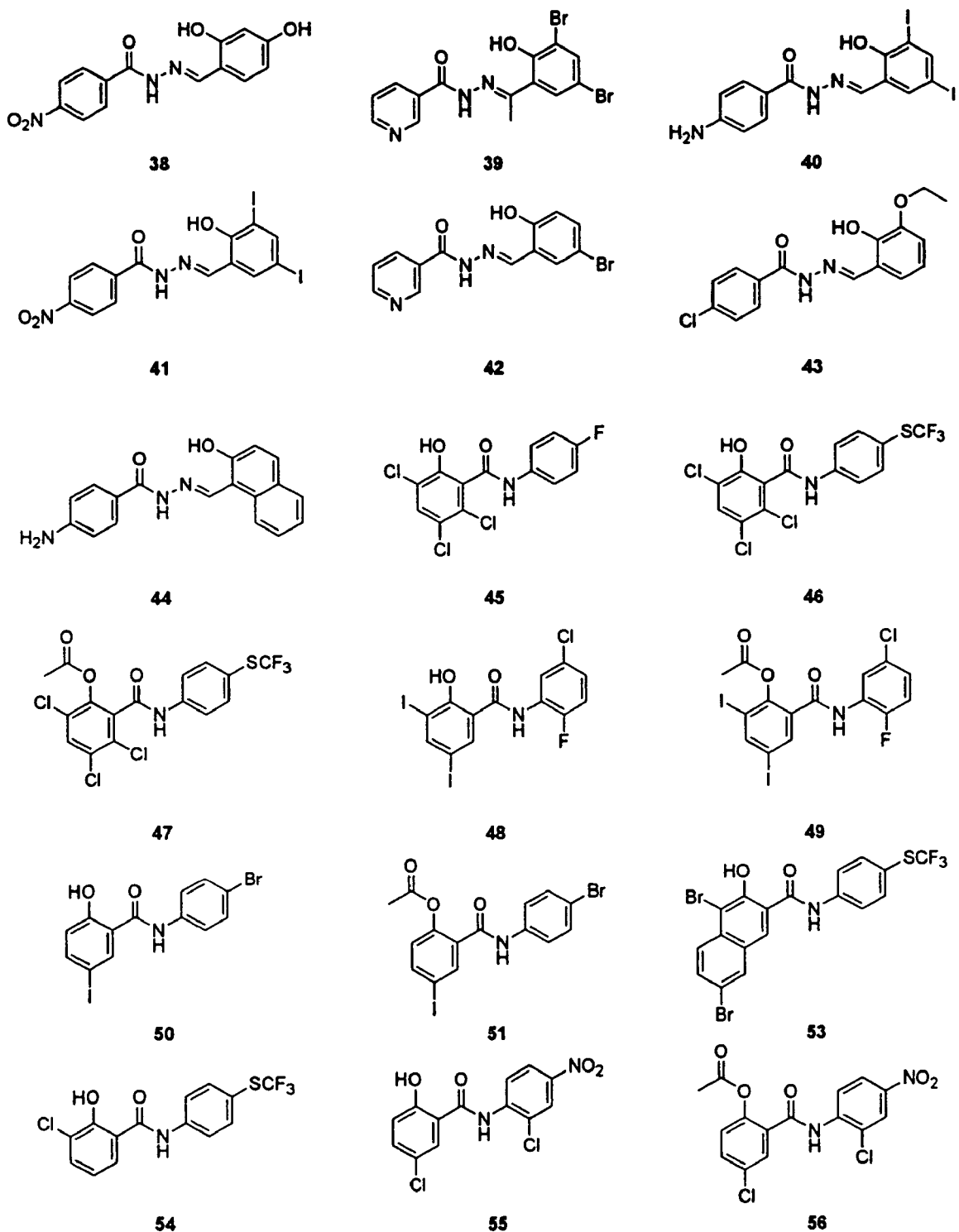
Figure 11:
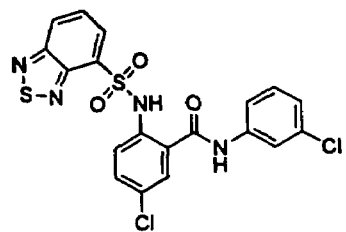
Figure 11:
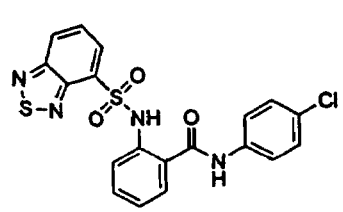
Figure 11:
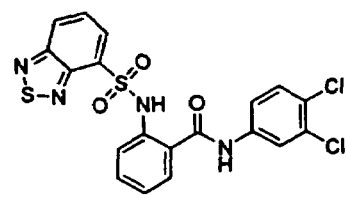
Figure 11:
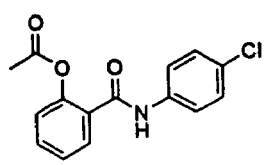
Figure 11:
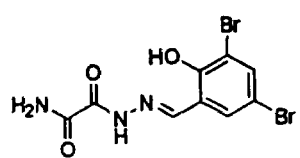
Figure 11:
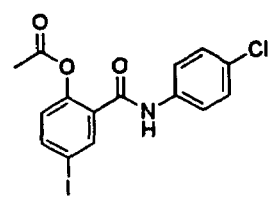

(B) A Schematic representation of reporter gene constructs for identification of inhibitors or activators of Yersinia type III secretion;

FIGS. 2A,B Screening readout obtained when performing the assay with bacteria (pIB29EL) alone in absence or presence of $Ca^{2+}$;

(A) Photo of wells from an assay 96-well plate that contain bacteria in absence or presence of $Ca^{2+}$;

(B) Quantification of the light signals in absence (black bar) or presence (white bar) of $Ca^{2+}$;

FIG. 3. Inhibition of the luciferase reporter gene light signal in the strain pIB29EL by a mouse monoclonal anti-YopB antibody added intermittently during the assay process;

FIG. 4A-C Inhibition of luciferase light emission (black bars) and bacterial growth (white bars) for the non-virulent screening strain pIB29EL in presence of different concentrations of compounds of the invention;

FIG. 5A-C Inhibition of luciferase light emission in different wild-type bacteria (p102EL, black bars; pIB102AL, white bars; pIB102FΔhlhL, grey bars; pIB102FL, striped) in the presence of different concentrations of compounds 3-5;

FIGS. 6A,B Inhibition of Yop secretion by compound 3 Yop secretion from the wild-type strain pIB102EL in presence of various concentrations of 3 investigated with Western analysis.

(A) Analysis of secreted Yops present in the surrounding medium;

(B) Analysis of total intracellular and medium Yop content;

FIGS. 7-11 Structural formulae of compounds according to the invention.

DESCRIPTION OF PREFERRED EMBODIMENTS

General. A compound collection consisting of 9,400 unique substances (ChemBridge, DiverSet F) was screened for inhibition of the luxAB reporter signal using the non-virulent strain pIB29EL. The compounds were screened in duplicate at a final concentration of 20 μg/mL. Assay interfering compounds, e.g. potential luciferase inhibitors, were identified by addition of hits from the primary screen to assay wells 10-20 min prior to addition of n-decanal. Compounds showing activity in one of the duplicate wells were re-screened to confirm activity or the lack thereof. The complete screening campaign gave about 60 compounds that caused at least 40% inhibition (duplicate average) of the luciferase light signal. For most of these compounds a dose/response relationship was established, and inhibition of bacterial growth was examined. A number of the compounds were found to have an $IC_{50}$ for inhibition of the luciferase light signal of 50 µM or less. Compounds 3-5 are representative examples of compounds that show a clear selectivity for inhibition of the luciferase light signal over growth inhibition indicating that these substances possibly act on targets directly or indirectly regulating expression of the Yops, but are not required for growth (FIG. 4A-C). Several of the compounds from the primary screening belong to a class of acylated hydrazones of salicylic aldehydes of which compound 3 is the most potent. The bacterial targets for compounds 3-5 are unknown but compounds closely related to 4 have been found to inhibit bacterial two-component systems[29].

Figure 1A:
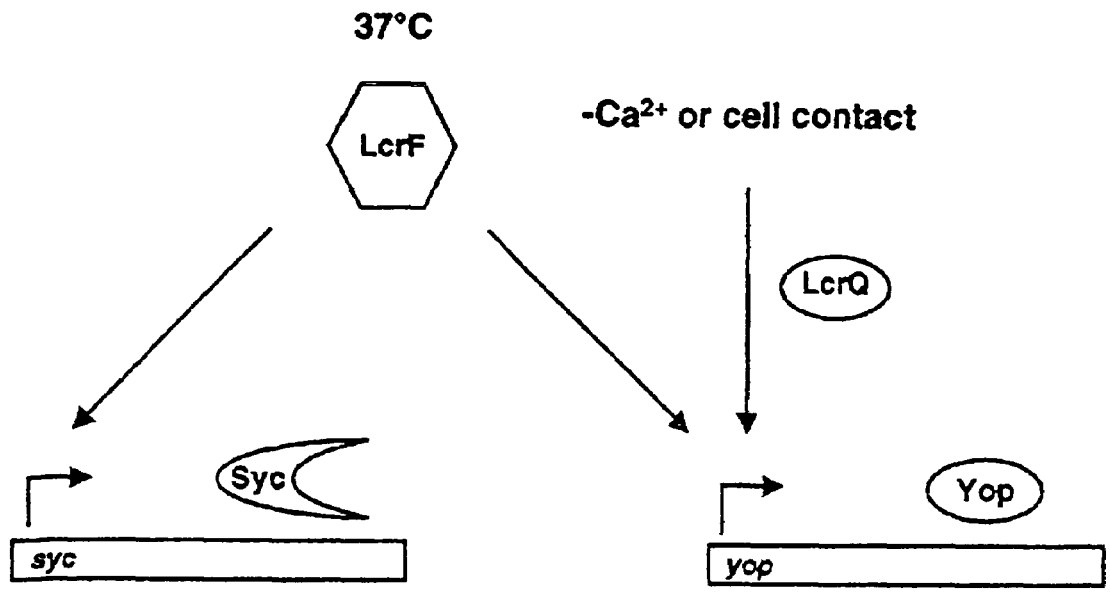
FIGS. 1A,B (A) The current model for regulation of Yop and Syc expression involving temperature and $Ca^{2+}$ dependence via the positive element LcrF and the negative element LcrQ.
Figure 1B:
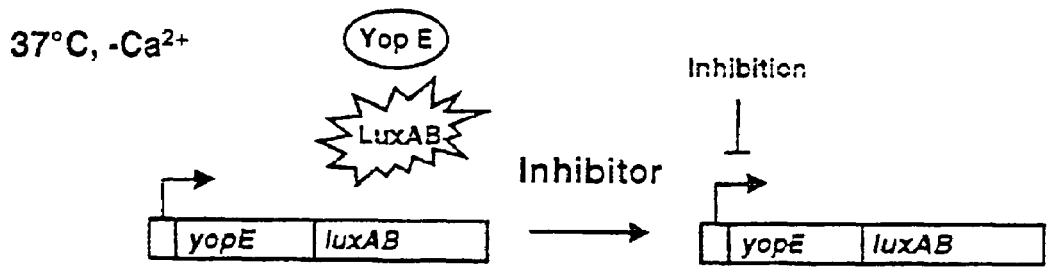
Figure 1B:
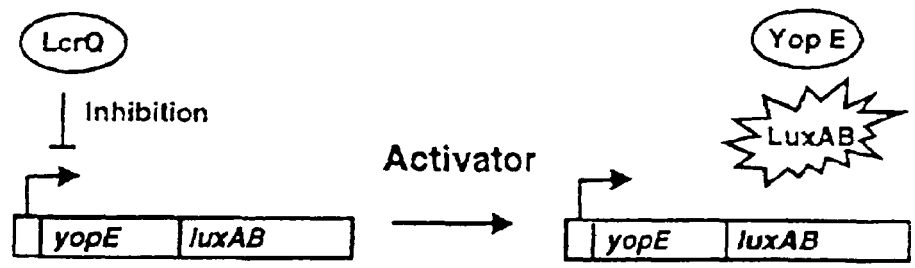

Detailed investigations were also carried out for the majority of the active compounds although most emphasis was put on compounds 3-5. All experiments based on luciferase-based readout were carried out in triplicate or quadruplicate in the same manner as in primary screening. As a first step the compounds were assayed with the wild-type control strain, pIB102AL, with luxAB downstream of the promoter for YerA, the chaperone for YopE. As seen in FIGS. 5A and 5B compounds 3 and 5 show a stronger inhibitory effect on the wild-type strain pIB102EL with luxAB under control of the YopE promoter than on the control strain. This selectivity suggests that compounds 3 and 5 target secretion or the $Ca^{2+}$ dependent regulation involving LcrQ rather than the temperature dependent LcrF cascade (cf. FIG. 1A). Compound 4 on the other hand show no selectivity for any of these two strains as illustrated in FIG. 5C.

In order to zoom in on potential targets and to further support a selective mode of action for compounds 3-5 two additional reporter gene strains were employed. Based on the regulatory model in FIG. 1A compounds that inhibit the signal from the yerA reporter gene should also inhibit a reporter gene signal under control of the LcrF promoter. The yopE and yerA promoters are both positively regulated by LcrF but the yerA promoter is not regulated by the negative $Ca^{2+}$ control loop. In pIB102FΔhlhL the protein LcrF lacks a negative self-regulating helix-loop-helix sequence thus resulting in enhanced levels of LcrF. Consistent with the regulatory model in FIG. 1A compound 4 inhibits the reporter gene signal all four strains pIB102EL, pIB102AL, pIB102FL, and pIB102FΔhlhL strains to more or less the same extent (FIG. 5C). These results suggest that compound 4 targets LcrF directly or act on regulatory elements upstream LcrF. Compound 3 on the other hand was found to enhance the reporter gene signal from both pIB102FL, and pIB1102FΔhlhL. The effect was most dramatic for pIB102FΔhlhL for which the signal was more than doubled at concentrations that almost completely inhibit the signal from pIB102EL (FIG. 5A). Compound 5 displays yet a different pattern showing minor inhibition of the signal from pIB102FL and modest enhancement of the signal for pIB1102FΔhlhL (FIG. 5B).

The investigation was continued by Western analysis of inhibition of actual Yop secretion in presence of compounds 3-5. The wild-type strain pIB102EL was grown at ambient temperature (ca. 21° C.) in presence or absence of different compound concentrations for one hour and then the temperature was raised to 37° C. for induction and secretion of the Yops. After three hours at 37° C. the bacteria were removed by centrifugation, and the protein content in the supernatant, i.e. the surrounding media, was examined by Western analysis using a polyclonal serum active against all secreted proteins. As seen in FIG. 6A compound 3 efficiently inhibits Yop secretion in a dose dependent manner similar to the light inhibition data obtained using the strain with luxAB under the YopE promoter. This dose dependent inhibition of secretion was also observed for compound 4 and 5, i.e. $IC_{50}$ for inhibition of the luciferase readout is similar to the $IC_{50}$ for inhibition secretion (data not shown). For compound 3 the total Yop content, i.e. Yops present in both bacteria and the surrounding media, was examined at various compound concentrations. As seen in FIG. 6B Yops can be observed at concentrations that completely inhibit secretion suggesting that compound 3 targets events in the actual secretion rather than Yop transcription or translation, i.e. the bands in the 50 and 100 µM lanes originate from intracellular proteins.

Bacterial strains and growth condition. All strains used are *Y. psedotuberculosis* serotype III (YPIII) and in the following text strains are only labelled with the name of the virulence plasmid. Strains with the luxAB contruct were prepared from either the non-virulent YopH and yadA mutant *Y. pseudotuberculosis* pIB29[28] or the wild type YadA mutant pIB102[27] by constructing yopE-luxAB, yer-luxAB, lcrF-luxAB and lcrFΔhlh-luxAB operon fusions essentially as described previous[26]. The resulting strains pIB29EL (yopE-luxAB), pIB29AL (yerA-luxAB), pIB102EL (yopE-luxAB, wild-type), pIB102AL (yer-luxAB, wild-type), pIB102FL (lcrF-luxAB, wild-type), and pIB1102FΔhlhL (lcrFΔhlh-luxAB, wild-type) strains were struck and grown at room temperature on LB-plates containing chloramphenicol (Sigma) at a final concentration of 50 μg/mL. From plates not older than one week, bacteria for experiments were grown in liquid brain/heart infusion (BHI) broth (Oxoid; Unipath Ltd., Basington, UK) containing 2.5 mM $CaCl_2$ or 20 mM $MgCl_2$ and 5 mM EGTA for $Ca^{2+}$ depletion.

Compounds, antibiotics and antibodies. The chemical library that consists of 9,400 unique compounds in 96-well plate format was purchased from ChemBridge (Diverset F). The compounds were dissolved in DMSO to give a stock solution of 2 mg/mL. For compounds further characterized in the described experiments additional 5 or 10 mg samples were purchased from ChemBridge. Streptomycin (Sigma), carbenicillin (Sigma), polymyxin B (mixture of polymyxin B1 and B2, Fluka), and nalidixic acid (Sigma) were dissolved in water. Antibodies against the different *Yersinia* proteins were available from other projects at the department of Molecular Biology, Umeå University.

The synthesis of compound 5 has been reported previously (2-[Benzo-2,1,3-thiadiazole-4-sulfonyl)amino]benzoic acids as synthetic intermediates for antihelmintics. Mikhailitsyn F. S., Drusvyatskaya S. K., Uvarova, N. A, patent no. SU1685935; Search for new antiparasitic agents 3. Synthesis of haloid-containing sulfamidobenzamides with benzo-2,1,3,-dithiazole residue in sulfonamide group and study of their acute toxicity. Mikhailitsyn F. S., Lebedeva M. N., Kozyreva N. P., Lychko N. D. Drusvyatskaya S. K., Uvarova, *Med. Parazitol. Parazit. Bolezni.* 1991 (2) 36-38). Acylated hydrazones of salicylaldehyde e.g. compound 3 and analogs are prepared from the corresponding acylhydrazides and aldehydes as described previously (Cytotoxicity of salicylaldehyde benzoylhydrazone analogs and their transition metal complexes: quantitative structure-activity relationships. Ainscough E. W, Brodie A. M., Denny W. A., Finlay G. J., Gothe S. A., Ranford J. D., *J. Inorg. Biochem.* 1999 (77) 125-133). Compound 4 and analogs are prepared according to a known method (Method of producing 2-acetoxy-4'-chloro-3,5-diiodobenzanilide. Mikhailitsyn F. S., Petyrov Y. F., Sapozhnikova L. A., USSR patent no. SU 1226807).

General screening and assay conditions. An overnight culture grown at room temperature in BHI medium containing 20 mM $MgCl_2$ and 5 mM EGTA for $Ca^{2+}$ depletion was diluted to $OD_{600}$=0.15-0.25. In parallel the compounds to be tested were dispensed into the wells of a 96-well plate (Polysorp FluoroNunc™ Modules, Nunc) containing 50 µL of medium per well. To each well 50 µL of the bacterial solution was added. For compounds dissolved in DMSO the final DMSO concentration was kept below 2%. The plate was incubated on an orbital shaker at room temperature (ca. 21° C.) for 1 h. The temperature was then shifted to 37° C. and incubation with orbital shaking was continued for 2 h. Subsequently the temperature was shifted back to room temperature and the plate was incubated for 2 h without shaking. Finally 100 µL freshly made n-decanal emulsion (Sigma, 10 µL/100 mL water, emulsified by vigorous shaking) was added to each well and the light emission was measured within 1-3 minutes after addition. Light emission was recorded with a light-sensitive charge-coupled device (CCD) camera, DIANA Chemoluminescense detection module (Raytest, Isotopenmessgeräte, GmbH). The intensity of the light signals was quantified using the computer program TINA (version 2.0). Primary screening of the compound library was carried out in duplicate with a final concentration of 20 µg/mL. Other experiments were carried out in triplicate and quadruplicate with modifications as indicated in the text and figure legends. For antibody experiments 5 µL monoclonal mouse ascites solution was used. Results were typically reproduced in at least three independent experiments.

Growth inhibition experiments. Growth inhibition by compounds identified in the screening process was measured by growing bacteria at 37° C. in the presence of different compound concentrations in 96-well plates containing 100 µL bacterial culture in BHI medium with 2.5 mM $CaCl_2$ per well. The experiments were carried out in a Molecular Device Spectramax 340 plate reader with continuous shaking at 37° C. and periodical determination of absorption at 600 nm. Experiments were carried out in triplicate or quadruplicate, and the results were typically reproduced in at least three independent experiments. Values for percent growth inhibition were calculated from differences in growth rate in presence or absence of compound over a time period with approximately linear growth.

Western analysis of protein secretion. An overnight culture grown at room temperature in BHI medium containing 20 mM $MgCl_2$ and 5 mM EGTA for $Ca^{2+}$ depletion, was diluted to $OD_{600}$=0.15-0.25. In parallel the compounds to be tested were dispensed into the wells of a 96-well plate containing 50 µL of medium per well. To each well 50 µL of the bacterial solution was added. The plate was incubated on an orbital shaker at room temperature for 1 h. The temperature was then shifted to 37° C. and incubation with orbital shaking was continued for 3 h. Subsequently the cultures were transferred to micro-centrifuge tubes. After brief centrifugation the supernatants were investigated by standard western analysis (12% SDS-PAGE) using a rabbit polyclonal total ant-Yop serum.

Motility Agar Assay

Motility was measured as the movement of bacterial cells through semisolid motility agar (Luria broth containing 0.25% Bactoagar). Around $10^7$ *Y. pseudotuberculosis* YPIII pIB102EL bacteria in a 2.5 μl drop were placed at the centre of each well in a 6-well plate (Falcon Multiwell) containing 5 ml motility agar supplemented with 5 mM EGTA, 20 mM $MgCl_2$ and different concentrations of test substance in 0.1 ml DMSO per well. The plates were incubated at 22° C. for 18 h to allow for the bacteria to grow and to move out from the centre of the plate. To induce Yop and LuxAB expression, plates were shifted to 37° C. (at this temperature flagellum production stops) and incubation was continued for 3 h. By placing 5 μl of n-decanal in the lid over each well to expose the bacteria to decanal fumes, light emission from the bacteria was induced. Emitted light was monitored and quantified using a charge-coupled device (CCD) camera. Immediately after measurement of light emission, a picture was taken in visible light to document the bacterial migration. Migration was then quantified directly from the picture as the diameter of the zone covered by bacteria.

REFERENCES

1. Finch, R. G. Antibiotic resistance. *J. Antimirobial Chemother.* 42,125-128 (1998).
2. Chin, G. J., Marx, J. & Eds. Resistance to antibiocics. *Science* 264, 359-393 (1994).
3. Cohen, M. L. Changing patterns of infectious disease. *Nature* 406, 762-767 (2000).
4. An, H. & Cook, P D. Methodologies for generating solution-phase combinatorial libraries. *Chem. Rev.* 100, 3311-3340 (2000).
5. Cork, D. & Hird, N. Work-up strategies far high-throughput solution synthesis. *Drug Discovery Today* 7, 56-63 (2002).
6. Lou, B. Navel strategies far solid-phase construction of small-molecule combinatorial libraries. *Drug Discovery Today* 6, 1288-1294 (2001).
7. Buysse, J. M. The role of genomics in antibacterial target discovery. *Curr. Med. Chem.* 8, 1713-1726 (2001).
8. McDevitt, D. & Rosenberg, M. Exploiting genomics to discover new antibiotics. *Trends Microbiol.* 9, 611-617 (2001).
9. Sundberg, S. A. High-throughput and ultra-high throughput screening: solution- and cell-based approaches. *Curr. Opin. Biotechnol.* 11, 47-53 (2000).
10. Hertzberg, R. P. & Pope, A. J. High-throughput screening: new technology for the 21st century. *Curr. Opin. Chem. Biol.* 4, 445-451 (2000).
11. Trias, J. The role of combichem in antibiotic discovery. *Curr. Opin. Microbiol.* 4, 520-525 (2001).
12. Goldschmidt, R. M., Macielag, M., Hlasta, D. J. & Barrett, J. F. Inhibition of virulence factors in bacteria. *Curr. Pharm. Design* 3, 125-142 (1997).
13. Alksne, L. E. & Projan, S. J. Bacterial virulence as target for antimicrobial chemotherapy. *Curr. Opin. Biotechnol.* 11, 625-636 (2000).
14. Stockwell, B. R. Frontiers in chemical genetics. *Trends Biotechnol.* 18, 449-455 (2000).
15. Shogren-Knaak, M. A., Alaimo, P. J. & Shokat, K. M. Recent advances in chemical approaches to the study of biological systems. *Anml. Rev. Cell Dev. Biol.* 17, 405-433 (2001).
16. Cornelis, G. R. & Wolf-Watz, H. The *Yersinia* Yop virulon: A bacterial system for subverting eukaryotic cells. *Mol. Microbiol.* 23, 861-867 (1997).
17. Cornelis, G. R. Molecular and cell biology aspects of plague. *Proc. Nat. Acad. Sci. USA* 97, 8778-8783 (2000).
18. Hueck, C J. Type III protein secretion systems in bacterial pathogens of animals and plants. *Microbiol. Mol. Biol. Rev.* 62, 379-433 (1998).
19. Cornelis, G. R. & Gijsegem, F. V. Assembly and function of type III secretory systems. *Annu. Rev. Microbiol.* 54, 735-774 (2000).
20. Galimand, M. et al. Multidrug resistance in *Yersinia pestis* mediated by a transferable plasmid. *New England J. Med.* 337, 677-680 (1997).

21. Guiyoule, A. et al. Transferable plasmid-mediated resistance to streptomycin in a clinical isolate of *yersinia pestis*. *Emerging Inf. Disease* 7, 43-48 (2001).
22. Hawley, R. J. & Eitzen Jr., E. M. Biological weapons—a primer for microbiologists. *Annu. Rev. Microbiol.* 55, 235-253 (2001).
23. Inglesby, T. V. et al. Plague as a biological weapon. *JAMA* 283, 2281-2290 (2000).
24. Achtman, M. et al. *Yersinia pestis*, the causative agent of plague, is a recently emerged clone of *yersinia pseudotuberculosis*. *Proc. Nat. Acad. Sci. USA* 96, 14043-14048 (1999).
25. Olsson, O., Koncz, C. & Szalay, A. A. The use of the luxA gene of the bacterial luciferase operon as a reporter gene. *Mol. Gen. Genet.* 215, 1-9 (1988).
26. Forsberg, A. & Rosqvist, R. In vivo expression of virulence genes of *yersinia pseudotuberculosis*. *Inf. Agents Disease* 2, 275-278 (1994).
27. Bölin, I. & Wolf-Watz, H. Molecular cloning of the temperature-inducible outer membrane protein 1 of *Y. pseudotuberculosis*. *Infect. Immun.* 43, 72-78 (1984).
28. Bölin, I. & Wolf-Watz, H. The plasmid-encoded Yop2b protein of *Yersinia pseudotuberculosis* is a virulence determinant regulated by calcium and temperature at the level of transcription. *Mol. Microbiol.* 2, 237-245 (1988).
29. Macielag, M. J. et al. Substituted salicylanilides as inhibitors of two-component regulatory systems in bacteria. *J. Med. Chem.* 41, 2939-2945 (1998).

TABLE 1

Inhibitory effect of known antibacterial agents[a]

| Antibiotic | Bacterial target | $IC_{50}$ (μM)[b] |
| --- | --- | --- |
| Carbenicillin | Transpeptidase | 15 |
| Streptomycin | 30S Ribosomal subunit | 4 |
| Nalidixic acid | DNA topoisomerase | 15 |
| Polymixin B | Membrane organization | 0.15 |

[a]Experiments were carried out with the non-virulent screening strain pIB29EL containing the yopE-luxAB construct.
[b]Concentration resulting in 50% reduction of luciferase light emission under screening conditions.

TABLE 2A

Electrospray mass spectroscopy (ESMS) data and inhibition of the luciferase light signal from pIB29EL at the indicated concentrations.

| | ESMS (M+H[+]) | | Inhibition (%) | | | |
| --- | --- | --- | --- | --- | --- | --- |
| Compound | Calculated | Observed | 10 | 20 | 50 | 100 μM |
| 3 | 444.0 | 444 | 12 | 48 | 85 | 86 |
| 7 | 400.0 | 400 | 25 | 20 | 68 | 93 |
| 9 | 291.3 | 291 | 9 | 21 | 41 | 49 |
| 10 | 325.3 | 326 | 30 | 49 | 56 | 57 |
| 11 | 386.4 | 386 | 30 | 42 | 69 | 80 |
| 12 | 247.2 | 247 | 12 | 16 | 41 | 65 |
| 13 | 323.3 | 323 | 26 | 47 | 69 | 73 |
| 5 | 512.8* | 513* | 35 | 60 | 69 | 66 |
| 17 | —# | —# | 36 | 42 | 89 | 90 |
| 18 | —# | —# | 11 | 51 | 70 | 62 |
| 19 | —# | —# | 0 | 0 | 45 | 70 |

TABLE 2B

Electrospray mass spectroscopy (ESMS) data and inhibition of the luciferase light signal from pIB29EL at the indicated concentrations.

| | ESMS (M+H[+]) | | Inhibition (%) | | | |
| --- | --- | --- | --- | --- | --- | --- |
| Compound | Calculated | Observed | 5 | 5 | 10 | 20 μM |
| 4 | 542.5 | 543 | 15 | 45 | 81 | 96 |
| 16 | —# | —# | 65 | 97 | 98 | 97 |

*(M–H)[+].
$^1$H NMR data δ ppm: 17: (CDCl$_3$)8.27(d, 1H), 8.00(d, 1H), 7.70(s, 1H), 7.56-7.48(m, 2H), 7.06(t, 2H), 2.37(s, 3H); 18: (CDCl$_3$)8.26(d, 1H), 8.02 (d, 1H), 7.73(s, 1H), 7.55(d, 2H), 7.37(t, 2H), 7.18(t, 1H), 2.36(s, 3H); 19: (DMSO-D$_6$)10.31(s, 1H), 8.18(d, 1H), 7.91(d, 1H), 7.64(t, 1H), 7.32-7.17 (m, 3H), 2.24(s, 3H); 16: (CDCl$_3$) 8.12(d, 1H), 7.96(s, 1H), 7.81(dd, 1H), 7.53(d, 2H), 7.33(d, 2H), 6.92(d, 1H), 2.32(s, 3H).

TABLE 2C

Electrospray mass spectroscopy (ESMS) data and inhibition of the luciferase light signal from pIB29EL or pIB102EL at the indicated concentrations.

| | ESMS | | Inhibition (%) | | | | | |
| --- | --- | --- | --- | --- | --- | --- | --- | --- |
| Comp. | (M–H[+]) Calc. | Obs. | 5 | 10 | 20 | 50 | 100 μM | Strain |
| 20 | —[1] | —[1] | —[2] | 2 | 5 | 19 | 48 | pIB29EL |
| 21 | —[1] | —[1] | —[2] | 21 | 18 | 44 | 57 | pIB29EL |
| 22 | 284.0 | 283.9 | 0 | 4 | 24 | 66 | 82 | pIB102EL |
| 23 | 373.9[3] | 373.7[3] | 70 | 75 | 83 | 80 | 78 | pIB29EL |
| 24 | —[1] | —[1] | 7 | 30 | 73 | 90 | 88 | pIB29EL |
| 25 | 497.8 | 497.5 | 80 | 92 | 93 | 100 | 98 | pIB29EL |
| 26 | 564.1 | 563.1 | 15 | 15 | 41 | 84 | 93 | pIB29EL |
| 27 | 387.9 | 387.7 | 9 | 3 | 1 | 13 | 20 | pIB29EL |
| 28 | 561.9 | 561.1 | 67 | 90 | 99 | 99 | 99 | pIB29EL |
| 29 | 519.9 | 519.9 | 19 | 18 | 21 | 30 | 28 | pIB29EL |
| 30 | —[1] | —[1] | 14 | 15 | 35 | 63 | 83 | pIB29EL |
| 31 | 463.9 | 463.5 | 10 | 30 | 60 | 77 | 98 | pIB29EL |
| 32 | 370.0 | 369.9 | 14 | 23 | 37 | 42 | 46 | pIB29EL |
| 33 | 605.8 | 605.7 | 71 | 70 | 68 | 69 | 71 | pIB29EL |
| 34 | 263.1[3] | 262.9[3] | 1 | 5 | 10 | 26 | 56 | pIB102EL |
| 35 | 309.0[3] | 308.8[3] | 0 | 0 | 5 | 21 | 43 | pIB102EL |
| 36 | 273.1* | 272.9[3] | 5 | 10 | 15 | 24 | 54 | pIB102EL |
| 37 | 313.2[3] | 312.9[3] | 5 | 8 | 21 | 30 | 32 | pIB102EL |
| 38 | —[1] | —[1] | 4 | 10 | 13 | 23 | 36 | pIB102EL |
| 39 | —[1] | —[1] | 0 | 3 | 4 | 13 | 24 | pIB102EL |
| 40 | 505.9 | 505.5 | 3 | 11 | 18 | 41 | 50 | pIB102EL |
| 41 | 535.9 | 535.5 | 3 | 13 | 33 | 48 | 44 | pIB102EL |
| 42 | 320.0[3] | 319.7[3] | 0 | 9 | 16 | 49 | 59 | pIB102EL |
| 43 | 319.1[3] | 318.8[3] | 0 | 6 | 12 | 22 | 34 | pIB102EL |
| 44 | 306.1[3] | 305.9[3] | 3 | 10 | 15 | 23 | 30 | pIB102EL |
| 45 | —[1] | —[1] | 0 | 0 | 3 | 30 | 65 | pIB29EL |
| 46 | —[1] | —[1] | 57 | 66 | 85 | 95 | 95 | pIB29EL |
| 47 | —[1] | —[1] | 55 | 61 | 73 | 90 | 90 | pIB29EL |
| 48 | 515.8 | 516.0 | 36 | 75 | 88 | 89 | 88 | pIB29EL |
| 49 | —[1] | —[1] | 24 | 34 | 63 | 89 | 88 | pIB29EL |
| 50 | —[1] | —[1] | 57 | 69 | 62 | 72 | 70 | pIB29EL |
| 51 | —[1] | —[1] | 91 | 87 | 89 | 87 | 85 | pIB29EL |
| 53 | —[1] | —[1] | 11 | 38 | 43 | 58 | 68 | pIB29EL |
| 54 | —[1] | —[1] | 41 | 63 | 86 | 89 | 87 | pIB29EL |
| 55 | —[1] | —[1] | 85 | 96 | 96 | 94 | 94 | pIB29EL |
| 56 | —[1] | —[1] | 77 | 90 | 91 | 91 | 90 | pIB29EL |
| 57 | —[1] | —[1] | 0 | 7 | 26 | 49 | 55 | pIB29EL |
| 58 | —[1] | —[1] | 4 | 5 | 10 | 11 | 15 | pIB29EL |
| 59 | —[1] | —[1] | 0 | 0 | 0 | 7 | 10 | pIB29EL |
| 60 | —[1] | —[1] | 0 | 21 | 65 | 89 | 89 | pIB29EL |
| 61 | —[1] | —[1] | 7 | 9 | 19 | 32 | 55 | pIB29EL |
| 62 | —[1] | —[1] | 95 | 92 | 91 | 91 | 90 | pIB29EL |

[1])$^1$H-NMR, 400Mhz, J in Hz
20 (CD$_3$)$_2$CO: δ 12.76(s, 1H), 12.19(s, 1H), 9.48(s, 1H), 8.22(d, 1H, J=8.69), 8.01-7.86(m, 4H), 7.66-7.54(m, 4H), 7.40(t, 1H, J=7.80), 7.23(d, 1H, J 8.78)

TABLE 2C-continued

Electrospray mass spectroscopy (ESMS) data and inhibition of the luciferase light signal from pIB29EL or pIB102EL at the indicated concentrations.

| Comp. | ESMS (M−H⁺) Calc. | Obs. | Inhibition (%) 5 | 10 | 20 | 50 | 100 μM | Strain |
|---|---|---|---|---|---|---|---|---|

21 (CD₃)₂CO: δ 14.17(s, 1H), 11.05(s, 1H), 8.38(d, 2H, J=8.69), 8.25(d, 2H, J=8.05), 7.80(d, 1H, J=2.29), 7.76(d, 1H, J=2.29), 2.63(s, 3H)
24 (CD₃)₂SO: δ 11.63(bs, 1H), 10.49(s, 1H), 7.92(dd, 1H, J=7.86 and 1.55), 7.75(d, 2H, J=8.96), 7.46-7.40(m, 3H), 7.00-6.93(m, 2H)
30 CDCl₃: δ 8.74(s, 1H), 8.53(t, 1H, J=8.15), 7.97(d, 1H, J=7.96), 7.21-7.04(m, 4H), 7.01(s, 1H), 2.42(s, 3H), 2.41(s, 3H)
38 (CD₃)₂CO: δ 11.64(s, 1H), 11.35(s, 1H), 8.91(s, 1H), 8.51(s, 1H), 8.39 (s, 1H), 8.22(s, 1H), 8.20(s, 1H), 7.20(d, 1H, J=8.32), 6.44(d, 2H, J=8.23)
39 (CD₃)₂SO: δ 14.45(s, 1H), 11.75(s, 1H), 9.08(s, 1H), 8.79(d, 1H, J 4.39), 8.28(d, 1H, J=7.78), 7.82(dd, 2H, J=9.97 and 2.01), 7.58(dd, 1H, J=7.96 and 4.94), 3.30(s, 2H), 2.51(s, 3H)
45 (CD₃)₂SO: δ 7.75-7.58(m, 3H), 7.23-7.10(m, 2H)
46 (CD₃)₂SO: δ 10.74(s, 1H), 7.88(s, 1H), 7.83(d, 2H, J=8.79), 7.72(d, 2H, J=8.59)
47 (CD₃)₂SO: δ 11.12(s, 1H), 8.24(s, 1H), 7.76(q, 4H, J=11.61), 2.67(s, 3H)
49 (CD₃)₂SO: δ 10.44(s, 1H), 8.39(d, 1H, 12.02), 8.02(d, 1H, J=1.92), 7.80(dd, 1H, J=6.50 and 2.38), 7.40-7.29(m, 2H), 2.25(s, 3H)
50 (CD₃)₂SO: δ 8.14(d, 1H, J=2.20), 7.71-7.65(m, 3H), 7.55(d, 2H, J=8.87), 6.81(d, 1H, J=8.60)
51 (CD₃)₂SO: δ 10.53(s, 1H), 7.99(d, 1H, J=1.93), 7.92(dd, 1H, J=8.42 and 2.11), 7.65(d, 2H, J=8.87), 7.53(d, 2H, J=8.78), 7.08(d, 1H, J=8.50), 2.18(s, 3H)
52 (CD₃)₂SO: δ 10.99(s, 1H), 8.50(d, 1H, J=1.92), 8.42(s, 1H), 8.17(d, 1H, J=9.15), 7.97(dd, 1H, J=9.06 and 1.92), 7.88(d, 2H, J=8.69), 7.74(d, 2H, J=8.69), 2.32(s, 3H)
53 (CD₃)₂SO: δ 11.17(bs, 1H), 8.50(s, 1H), 8.26(d, 1H, J=1.92), 8.01(d, 1H, J=9.06), 7.92(d, 2H, J=8.78), 7.83(dd, 1H, J=9.15 and 2.02), 7.77(d, 2H, J=8.69)
54 (CD₃)₂CO: δ 12.25(s, 1H), 10.82(s, 1H), 7.96(d,1H, J8.05), 7.89(d, 2H, J=8.60), 7.75(d, 2H, J=8.6), 7.67(dd, 1H, J=7.87 and 0.83), 7.01(t, 1H, J=7.86)
55 CD₃OD: δ 8.89(d, 1H, J=9.24), 8.39(d, 1H, J=2.56), 8.24(dd, 1H, 1=9.24 and 2.65), 8.07(d, 1H, J=2.74), 7.43(dd, 1H, J=8.69 and 2.74)
56 CDCl₃): δ 9.05(s, 1H), 8.84(d, 1H, J=9.24), 8.35(d, 1H, J 2.38), 8.22 (dd, 1H, J=9.15 and 2.29), 7.97(d, 1H, J=2.38), 7.55(dd, 1H, J=8.60 and 2.38), 7.18(d, 1H, J=8.69)
57 (CD₃)₂CO: δ 10.90(s, 1H), 9.56(s, 1H), 8.37(d, 1H, J=6.86), 8.28(d, 1H, J=8.96), 7.90-7.82(m, 2H), 7.76(s, 1H), 7.67(d, 1H, J=8.32), 7.61(d, 1H, J=8.14), 7.45(t, 1H, J=8.05), 7.26(d, 1H, J=8.05), 7.12(d, 1H, J 8.42)
58 (CD₃)₂CO: δ 10.69(s, 1H), 9.47(s, 1H), 8.31-8.20(m, 2H), 7.91(s, 1H), 7.81(dd, 1H, J=8.87 and 1.83), 7.74(d, 1H, 1=8.42), 7.65-7.56(m, 2H), 7.47-7.39(m, 2H), 7.25(d, 1H, J=7.78), 7.07(t, 1H, J=7.68)
59 (CD₃)₂CO: δ 10.64(s, 1H), 9.56(s, 1H), 8.29(d, 1H, J=7.23), 8.24(s, 1H, J=8.87), 8.06(d, 1H, J=2.20), 7.81(dd, 1H, J=8.78 and 1.74), 7.74(d, 1H, 1=8.42), 7.86(dd, 1H, J=8.78 and 6.40), 7.64-7.57(m, 2H), 7.47(m, 1H), 7.08(t, 1H, J=7.41)
60 (CD₃)₂SO: δ 10.48(s, 1H), 7.73(d, 2H, J=8.78), 7.68(dd, 1H, J=7.60 and 1.47), 7.58(dd 1H, J=7.96 and 1.56), 7.43-7.37(m, 3H), 7.26(dd 1H, J=8.14 and 0.82), 2.19(s, 3H)
61 (CD₃)₂SO: δ 12.83(s, 1H), 12.38(s, 1H), 8.65(s, 1H), 8.38(s, 1H), 8.03 (s, 1H), 7.84(d, 1H, J=2.10), 7.70(d, 1H, J=2.01)
62 CDCl₃: δ 8.13(d, 1H, J=2.11), 7.96(s, 1H), 7.82(dd, 1H, J=8.51 and 2.19), 7.53(d, 2H, J=8.69), 7.33(d, 2H, J=8.88), 6.92(d, 1H, J=8.60), 2.32 (s, 3H)

²⁾Not determined
³⁾(M+H)⁺,

The invention claimed is:

1. A compound selected from the group consisting of:

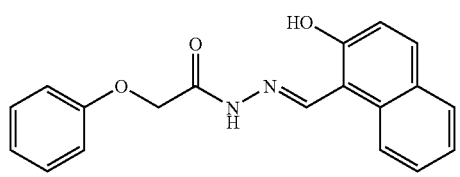

20

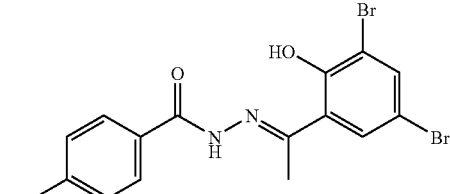

21

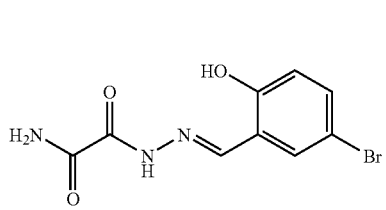

22

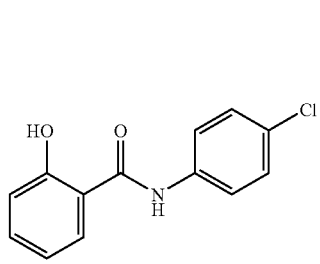

24

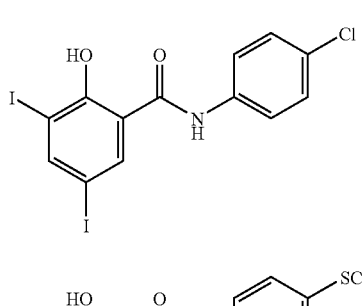

25

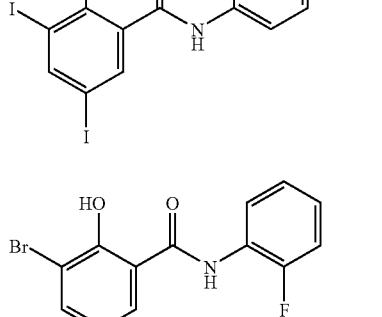

26

27

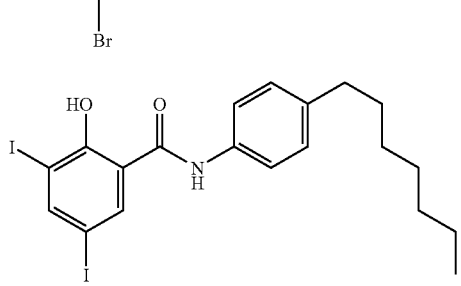

28

29 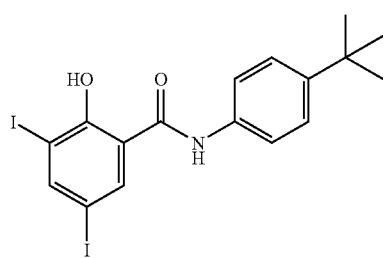
30 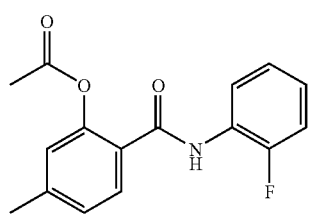
31 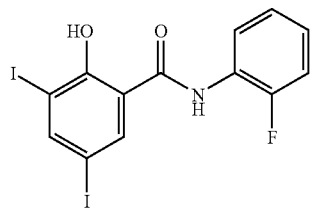
32 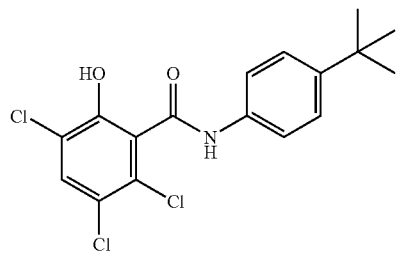
33 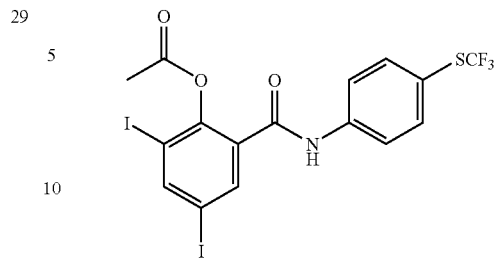
34 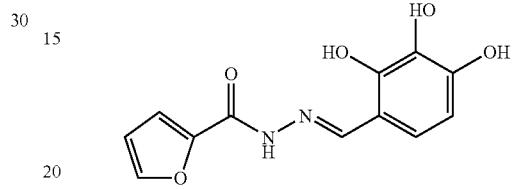
37 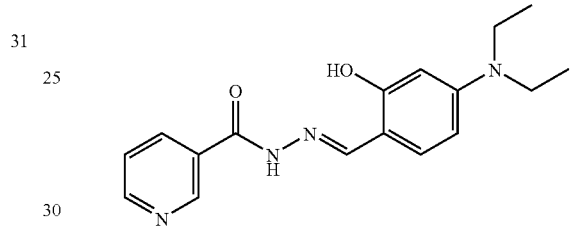
2. A compound according to claim 1 which is of formula 22.
3. A compound according to claim 1 which is of formula 25.
4. A compound according to claim 1 which is of formula 28.
5. A compound according to claim 1 which is of formula 30.
6. A compound according to claim 1 which is of formula 31.
* * * * *